United States Patent
Phillips et al.

(10) Patent No.: US 11,458,250 B2
(45) Date of Patent: Oct. 4, 2022

(54) SYSTEM AND TECHNIQUES FOR DRUG RESERVOIR VOLUME DETECTION

(71) Applicant: Insulet Corporation, Acton, MA (US)

(72) Inventors: Kenneth Phillips, Boston, MA (US); Steven Cardinali, Woburn, MA (US); David Nazzaro, Groveland, MA (US)

(73) Assignee: INSULET CORPORATION, Acton, MA (US)

( * ) Notice: Subject to any disclaimer, the term of this patent is extended or adjusted under 35 U.S.C. 154(b) by 447 days.

(21) Appl. No.: 16/428,294

(22) Filed: May 31, 2019

(65) Prior Publication Data

US 2019/0365990 A1   Dec. 5, 2019

Related U.S. Application Data

(60) Provisional application No. 62/678,344, filed on May 31, 2018, provisional application No. 62/773,634, filed on Nov. 30, 2018.

(51) Int. Cl.
| | |
|---|---|
| *A61M 5/168* | (2006.01) |
| *A61M 5/145* | (2006.01) |
| *G01F 23/263* | (2022.01) |
| *G01F 17/00* | (2006.01) |
| *A61M 5/142* | (2006.01) |

(52) U.S. Cl.
CPC ...... *A61M 5/1684* (2013.01); *A61M 5/14248* (2013.01); *A61M 5/14593* (2013.01); *G01F 17/00* (2013.01); *G01F 23/263* (2013.01); *A61M 5/14586* (2013.01); *A61M 2205/3317* (2013.01); *A61M 2205/3389* (2013.01); *A61M 2205/50* (2013.01)

(58) Field of Classification Search
CPC ......... A61M 5/1684; A61M 2205/3317; G01F 23/263
See application file for complete search history.

(56) References Cited

U.S. PATENT DOCUMENTS

| | | | | |
|---|---|---|---|---|
| 4,237,878 | A | * 12/1980 | Kobayashi | A61M 5/1684 604/122 |
| 5,135,485 | A | * 8/1992 | Cohen | A61M 5/1684 324/606 |
| 5,575,770 | A | 11/1996 | Melsky et al. | |
| 5,814,020 | A | 9/1998 | Gross | |

(Continued)

FOREIGN PATENT DOCUMENTS

| | | |
|---|---|---|
| JP | 2008536625 A | 9/2008 |
| JP | 2010510027 A | 4/2010 |

(Continued)

OTHER PUBLICATIONS

European Search Report and Written Opinion for the EP Application No. EP17736272, dated Oct. 7, 2019.

(Continued)

*Primary Examiner* — Jenna Zhang
(74) *Attorney, Agent, or Firm* — Goodwin Procter LLP

(57) ABSTRACT

Reservoir systems with improved wake up and fill volume detection techniques are provided. An example reservoir system may include a flexible reservoir and electrical components for detecting fill volume of the flexible reservoir without adversely affecting performance of the flexible reservoir when receiving or dispensing a liquid drug.

9 Claims, 19 Drawing Sheets

(56) References Cited

U.S. PATENT DOCUMENTS

| | | | |
|---|---|---|---|
| 5,876,377 A | 3/1999 | Kriesel | |
| 6,045,533 A | 4/2000 | Kriesel et al. | |
| 6,152,898 A | 11/2000 | Olsen | |
| 6,206,850 B1 | 3/2001 | ONeil | |
| 6,210,368 B1* | 4/2001 | Rogers | A61M 5/14593 604/131 |
| 6,666,852 B2 | 12/2003 | Niedospial, Jr. | |
| 7,220,245 B2 | 5/2007 | Kriesel | |
| 8,613,724 B2 | 12/2013 | Lanier, Jr. et al. | |
| 8,758,308 B2 | 6/2014 | Alferness et al. | |
| 2001/0034502 A1* | 10/2001 | Moberg | A61M 5/1456 604/67 |
| 2002/0066715 A1 | 6/2002 | Niedospial | |
| 2003/0120262 A1* | 6/2003 | Wieland | A61M 5/14276 604/891.1 |
| 2003/0136189 A1* | 7/2003 | Lauman | A61M 1/287 73/304 C |
| 2003/0139774 A1 | 7/2003 | Epstein et al. | |
| 2005/0238507 A1 | 10/2005 | Dilanni et al. | |
| 2006/0253088 A1 | 11/2006 | Chow et al. | |
| 2006/0282290 A1 | 12/2006 | Flaherty et al. | |
| 2007/0025811 A1 | 2/2007 | Wilhelm | |
| 2007/0112332 A1 | 5/2007 | Harding et al. | |
| 2008/0001737 A1 | 1/2008 | Metry | |
| 2008/0051765 A1 | 2/2008 | Mounce | |
| 2008/0065000 A1 | 3/2008 | Bidinger et al. | |
| 2008/0249508 A1 | 10/2008 | Lopez et al. | |
| 2011/0130742 A1 | 6/2011 | Hawkins et al. | |
| 2011/0231204 A1 | 9/2011 | De La Huerga | |
| 2012/0056000 A1 | 3/2012 | Shores | |
| 2016/0008536 A1 | 1/2016 | Gravesen et al. | |
| 2016/0144105 A1 | 5/2016 | Hooven et al. | |
| 2016/0296695 A1 | 10/2016 | Hassman et al. | |
| 2017/0340811 A1 | 11/2017 | Pananen | |
| 2019/0001057 A1* | 1/2019 | Tsoukalis | A61M 5/172 |

FOREIGN PATENT DOCUMENTS

| | | |
|---|---|---|
| WO | 2009070731 A1 | 6/2009 |
| WO | 2014154777 A1 | 10/2014 |
| WO | 2014204894 A2 | 12/2014 |
| WO | 2015061690 A1 | 4/2015 |
| WO | 2015177652 A1 | 11/2015 |

OTHER PUBLICATIONS

International Search Report and Written Opinion dated Feb. 13, 2009, issued in related International Patent Application No. PCT/US08/84971, 6 pages.

NovoLog, "NovoLog Flex Pen", available at http://www.novolog.com/devices-flexpen.asp; retrieved on Sep. 11, 2007.

International Search Report and Written Opinion dated Mar. 27, 2020, issued in related International Patent Application No. PCT/US19/42408, 18 pages.

International Search Report and Written Opinion for the International Patent Application No. PCT/US17/12207, dated May 26, 2017, 10 pages.

\* cited by examiner

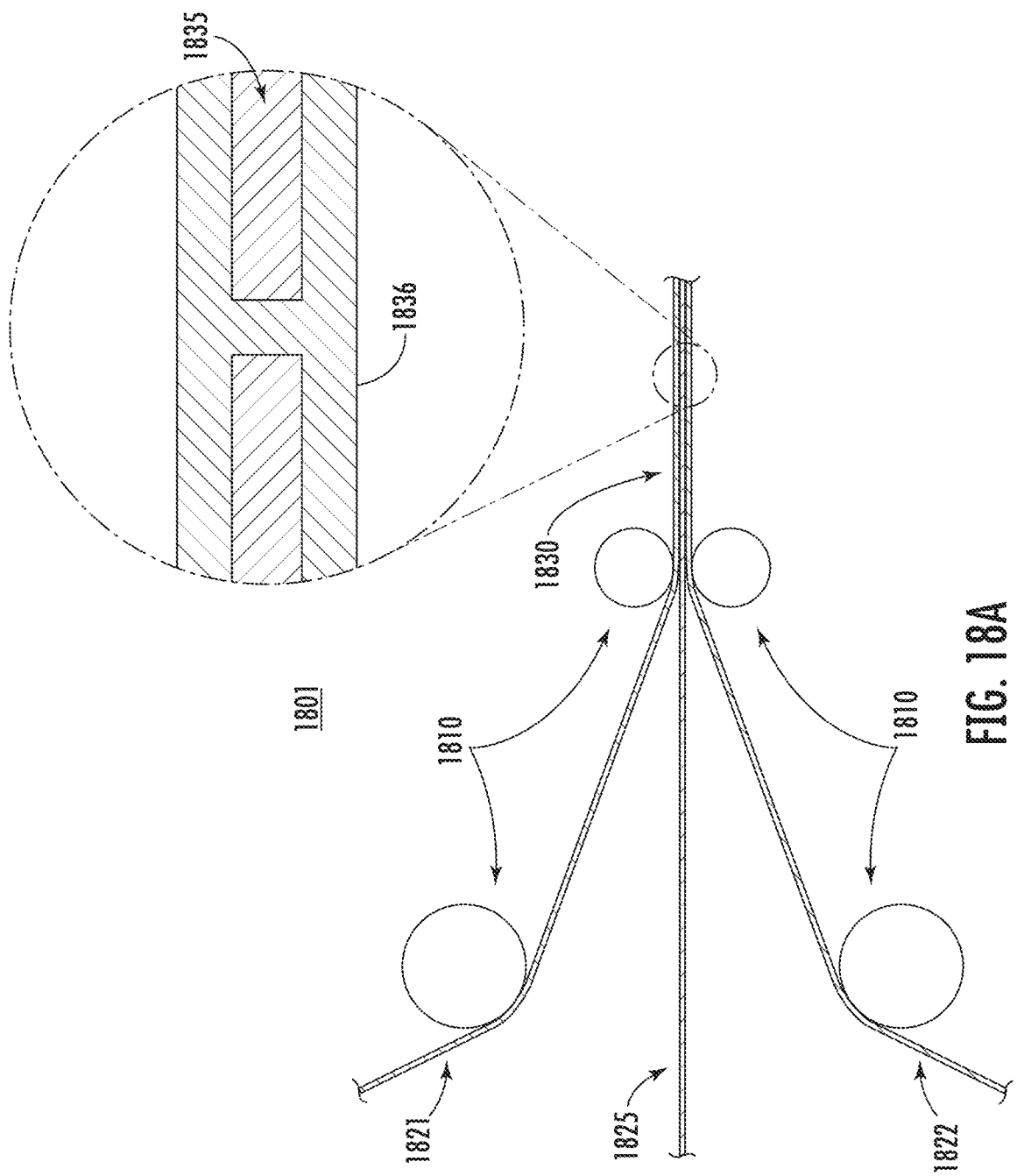

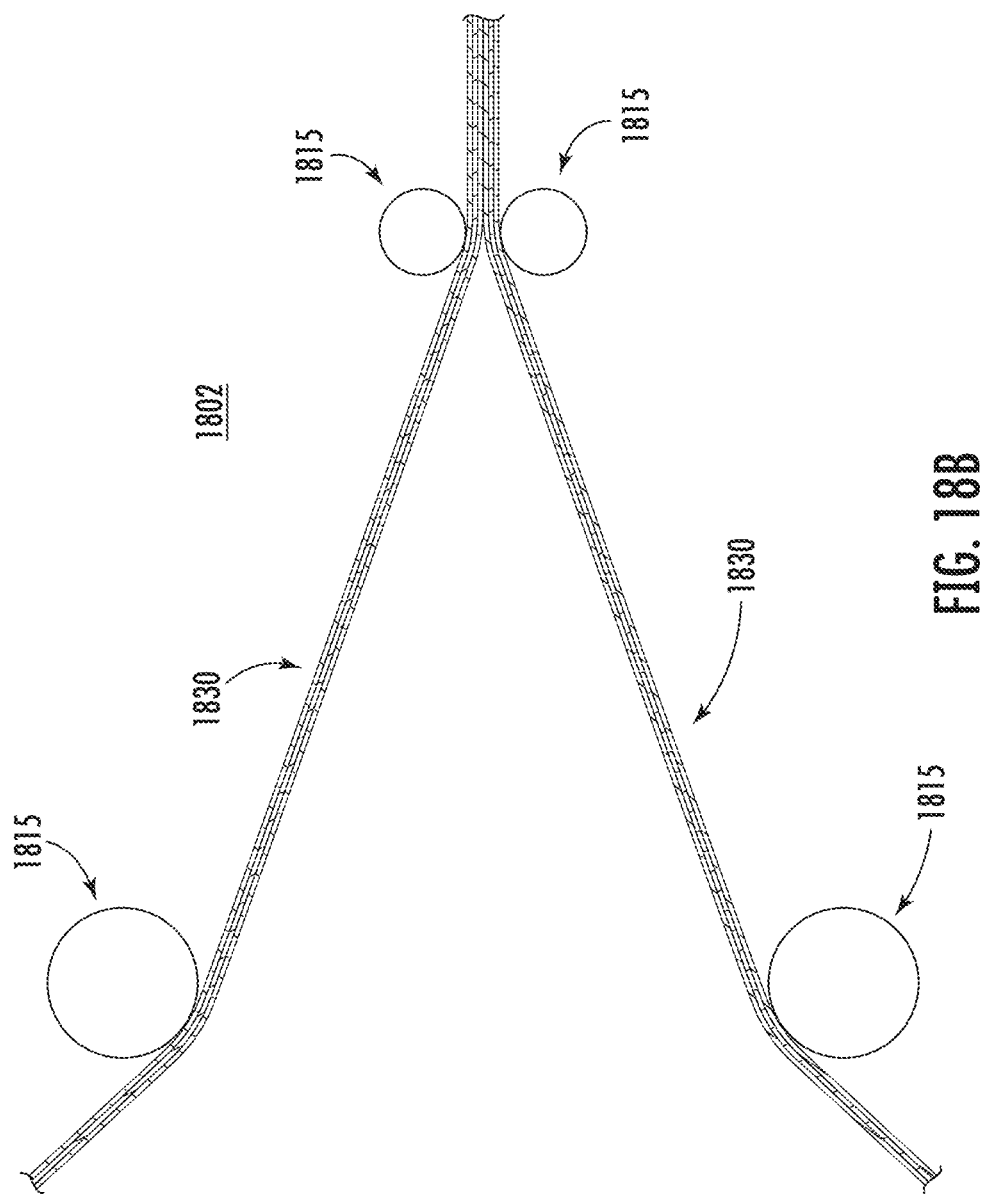

SYSTEM AND TECHNIQUES FOR DRUG RESERVOIR VOLUME DETECTION

CROSS-REFERENCE TO RELATED APPLICATION

This application claims priority to U.S. Provisional Patent Application No. 62/678,344, filed on May 31, 2018, and U.S. Provisional Patent Application No. 62/773,634, filed on Nov. 30, 2018, the entire contents of both applications are hereby incorporated by reference.

TECHNICAL FIELD

Examples generally relate to reservoirs for storing a liquid drug and more particularly to flexible reservoir systems for storing a liquid drug within a wearable drug delivery device.

BACKGROUND

In many conventional drug delivery systems, a rigid reservoir is used to store a liquid drug. A "fill rod" is commonly used with the rigid reservoir to determine when the rigid reservoir is filled with a minimum amount of the liquid drug. The fill rod is also used to detect when the rigid reservoir contains less than the minimum amount of the liquid drug, to enable a patient to be alerted that additional liquid drug may be needed.

Rigid reservoirs require a plunger to travel down the length of rigid reservoir to release the stored liquid drug. Further, rigid reservoirs are required to have a constant cross-section due to the necessity of the plunger traveling the length of the rigid reservoir. This requirement can lead to inefficiencies in volume usage of the rigid reservoir and consequently the drug delivery system.

Switching to a flexible reservoir that can contract as fluid is expelled can provide numerous benefits including, for example, allowing the drug delivery system to be packed more efficiently since the flexible reservoir can have a variable cross-section. However, the fill rod used with rigid reservoirs cannot be used with flexible reservoirs. Accordingly, there is a need for a new system, apparatus, and/or method for detecting fill volume of a flexible reservoir used with a drug delivery system. Typically, fill volume for a flexible reservoir is determined through the use of flow meters, orifice monitors, or pressure sensors. These devices can be effective; however, they often restrict the flow of a liquid drug, thereby reducing the efficiency of filling the flexible reservoir or extracting the liquid drug from the flexible reservoir. Accordingly, there is a need to detect fill volume of a flexible reservoir without reducing the ability of the flexible reservoir to receive or provide a liquid drug.

SUMMARY

A system is disclosed that includes a flexible reservoir, a fluid path component, a pair of capacitive sensing electrodes, a capacitive sensing component and a controller component. The fluid path component and the pair of capacitive sensing electrodes may be coupled to the flexible reservoir. The capacitive sensing component may be coupled to the pair of capacitive sensing electrodes and the controller component. The capacitive sensing component may be is operable to detect a capacitance between the pair of capacitive sensing electrodes.

Disclosed is another system including a flexible reservoir, a fluid path component, a capacitive pressure sensor, and a controller component. The fluid path component and the capacitive pressure sensor coupled to the flexible reservoir. The capacitive pressure sensor comprises a first electrode, a second electrode, an elastic component positioned between the first and second electrodes, a first lead component coupled to the first electrode, and a second lead component coupled to the second electrode. The controller component may be coupled to the first and second lead components and is operable to detect a capacitance between the first and second electrode and determine a volume of the flexible reservoir based on the detected capacitance between the first and second electrodes.

Disclosed is yet another system that includes a flexible reservoir, electrical contact elements coupled to the flexible reservoir, a fluid path component coupled to the flexible reservoir, a first clamp component positioned under the flexible reservoir, a second clamp component positioned over the flexible reservoir, and a controller component. The controller component may be coupled to the electrical contact elements.

BRIEF DESCRIPTION OF THE DRAWINGS

FIGS. 18A and 18B illustrate an example of a process for embedding electrodes into a side of an example of a reservoir.

DETAILED DESCRIPTION

This disclosure presents various systems, components, and methods related to reservoirs for drug delivery devices. Each of the systems, components, and methods disclosed herein provides one or more advantages over conventional systems, components, and methods.

Various examples provide improved reservoir systems. The reservoir systems include a flexible reservoir and electrical components for detecting fill volume of the flexible reservoir without adversely affecting performance of the flexible reservoir when receiving or dispensing a liquid drug.

In various examples, electrical contacts are selectively placed externally along the geometry of a flexible reservoir. The electrical contacts can enable device "wake up" detection and fill volume ("fuel gauging") detection without restricting flow of a liquid drug (e.g., when the flexible reservoir is being filled or drained). Techniques for fill volume detection disclosed herein can decouple fuel sensing from fixed geometry of the flexible reservoir. With knowledge of the profile of the flexible reservoir and how the flexible reservoir may expand, or inflate, when being filled, the electrical contacts can be arranged in a manner to enable fill volume to be detected.

In various examples, a reservoir is externally and selectively coated with electrical conductors in order to accurately sense fill volume by completing an electrical circuit or, alternatively, by breaking an electrical circuit. Fill volume detection can thereby be provided for a non-rigid container regardless of orientation. Connections with mating electrical contacts can be made or broken and can be sensed by a logic device (e.g., a controller or microprocessor) to determine fill volume.

Various examples provide detection of a fill volume for a flexible reservoir. The flexible reservoir can be used with a wearable drug delivery device. The flexible reservoir can store a liquid drug. Various examples provide systems, apparatuses, and/or methods for detecting a fill volume of the flexible reservoir, thereby enabling the amount of liquid drug stored in the reservoir to be determined.

Figure 1:
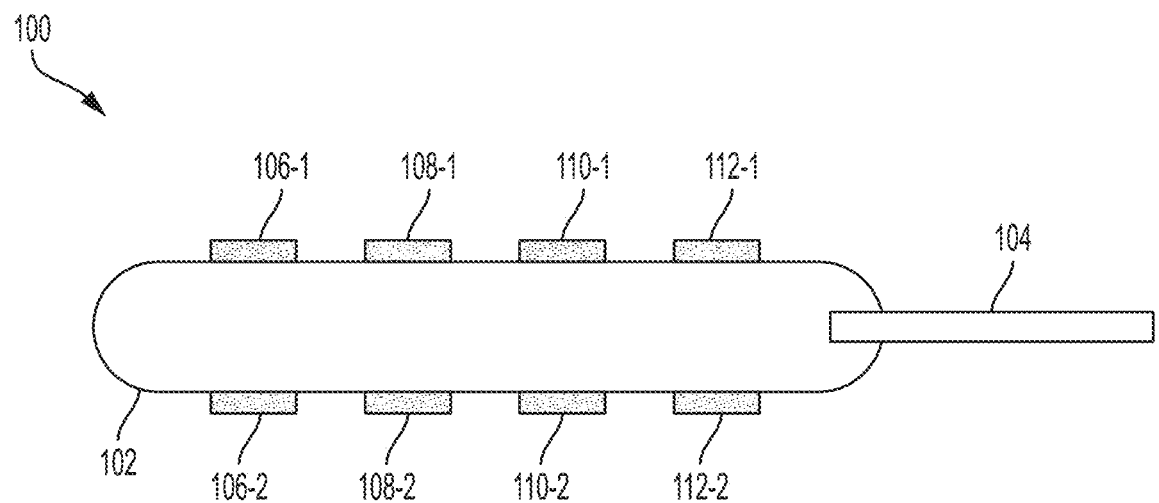
FIG. 1 illustrates an example of a system having a flexible reservoir with imbedded capacitive sensors for fill detection.

FIG. 1 illustrates an example of a system 100 having a flexible reservoir with imbedded capacitive sensors for fill detection. The system 100 can include a reservoir 102 and a fluid path component 104. The reservoir 102 can be a flexible reservoir. In various examples, the reservoir 102 can be made of a plastic material. A shape of the reservoir 102 can change (e.g., expand or contract) based on an amount of fluid stored in the reservoir 102. The fluid path component 104 can be coupled to the reservoir 102. A portion of the fluid path component 104 can extend into a cavity or interior of the reservoir 102. The fluid path component 104 can be formed of any material including, for example, plastic or metal. A liquid or fluid can enter or exit the reservoir 102 through the fluid path component 104.

The system 100 can further include capacitive sensing electrodes 106-1, 108-1, 110-1, and 112-1 positioned on a first side of the reservoir 102 and corresponding capacitive sensing electrodes 106-2, 108-2, 110-2, and 112-2 positioned on a second side of the reservoir 102. Specifically, the capacitive sensing electrode 106-1 is paired or corresponds with the capacitive sensing electrode 106-2, the capacitive sensing electrode 108-1 is paired or corresponds with the capacitive sensing electrode 108-2, the capacitive sensing electrode 110-1 is paired or corresponds with the capacitive sensing electrode 110-2, and the capacitive sensing electrode 112-1 is paired or corresponds with the capacitive sensing electrode 112-2.

Figure 2:
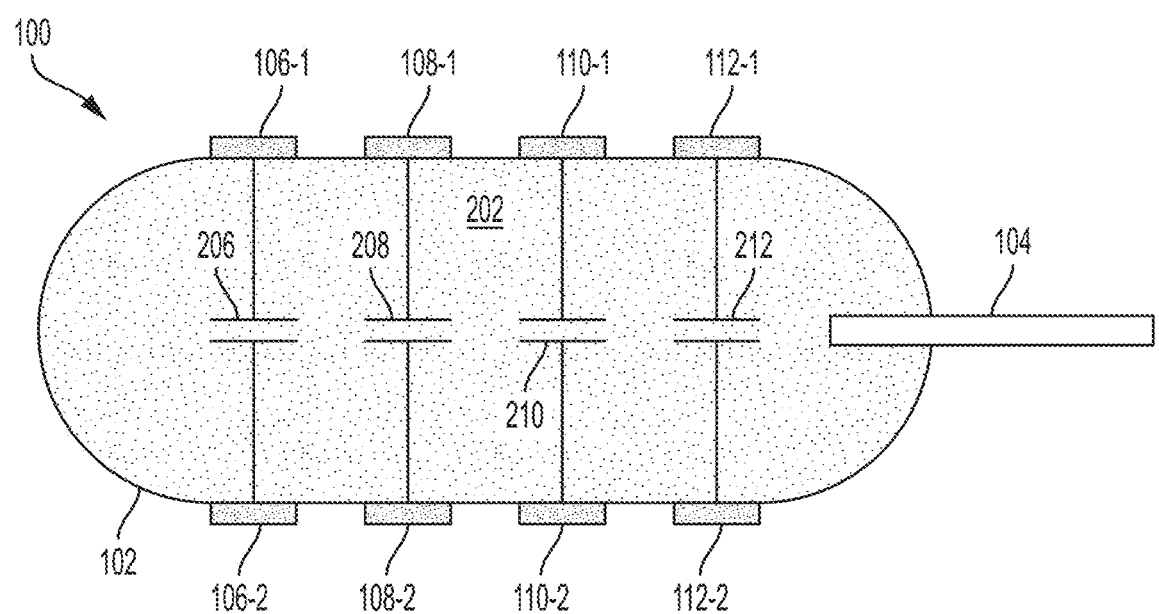
FIG. 2 illustrates the system example of FIG. 1 with the reservoir filled with a liquid or fluid.

The capacitive sensing electrode pairs 106-112 can be positioned on an outside or exterior surface of the reservoir 102, on an inside or interior surface of the reservoir 102, or within a material forming the reservoir 102, or any combination thereof. As shown in FIG. 2, four corresponding pairs of the capacitive sensing electrodes 106-112 are depicted but the system 100 is not so limited—that is, the system 100 can include any number of the capacitive sensing electrodes and/or any number of pairs of the capacitive sensing electrodes coupled to the reservoir 102.

The reservoir 102 can enlarge or expand when an interior of the reservoir 102 is filled with a liquid or fluid. FIG. 1 shows the reservoir 102 when the reservoir 102 is substantially empty. As the reservoir 102 expands when being filled or as the reservoir 102 becomes smaller when being emptied, the capacitive sensing electrodes 106-112 can be used to determine a volume of the reservoir 102 and, in turn, an amount of liquid contained within the reservoir 102. Specifically, the capacitive sensing component can detect a capacitance between capacitive sensing electrodes 106-112 (e.g., 106-1, 108-1, 110-1, 112-1) and the corresponding capacitive sensing electrodes 106-112 (e.g., 106-2, 108-2, 110-2, 112-2) to determine a size, shape, and/or volume of the reservoir 102 (e.g., a fill volume of the reservoir 102).

In an example, the capacitance between any respective pair of the capacitive sensing electrodes 106-112 can increase as the volume of the reservoir 102 gets smaller and can decrease as the volume of the reservoir 102 gets larger. The changes in voltage or current can be detected by the capacitive sensing electrodes 106-112 and provided to a controller for calculating the shape, size, and/or volume (e.g., fill volume) of the reservoir 102. In this way, the system 100 provides fill volume detection for the reservoir 102.

The system 100 can be made in a variety of ways. In various examples, the reservoir 102 can be formed from blow molded, Laser Direct Structuring (LDS)-capable plastic. A desired electrode structure can then be burned into the plastic by a laser with the plastic subsequently placed into a plating bath. Metal foil for forming the capacitive sensing electrode pairs 106-112 can be adhered to the plastic with a flexible adhesive, utilizing vapor deposition or the like. In another example, the capacitive sensing electrode pairs 106-112 may be made by die cutting the electrodes pairs from a conductive stock material. In yet another example, the reservoir 102 may be formed from an expandable silicon embedded with electrodes suitable to function as capacitive sensing electrodes or the like. In a further example, the reservoir 102 may be formed from a conductive material whose resistance or other properties change as the reservoir 102 expands while being filled with fluid or shrinks as fluid is dispensed. The change in resistance or other properties may be used to determine a volume of the fluid within the reservoir 102.

FIG. 2 illustrates an example of the system 100 with the reservoir 102 filled with a liquid or fluid 202. As shown in FIG. 2, each respective pair of the capacitive sensing electrode 106-112 are spaced further apart in comparison to the relative spacing shown in FIG. 2. Capacitors 206, 208, 210, and 212 are not hardware devices within the reservoir 102 but are merely illustrative and represent the capacitance (e.g., measured or detected) between a respective pair of the capacitive sensing electrode pairs 106-112. Specifically, in the example of FIG. 2, the capacitor 206 represents the measured or detected capacitance between the capacitive sensing electrode 106-1 and the capacitive sensing electrode 106-2, the capacitor 208 represents the measured or detected capacitance between the capacitive sensing electrode 108-1 and the capacitive sensing electrode 108-2, the capacitor 210 represents the measured or detected capacitance between the capacitive sensing electrode 110-1 and the capacitive sensing electrode 110-2, and the capacitor 212 represents the measured or detected capacitance between the capacitive sensing electrode 112-1 and the capacitive sensing electrode 112-2.

The measured capacitance values 206-212 can be monitored continuously or periodically. The measured capacitance values 206-212 can be provided to a controller or other electronic device component for determination of the fill volume of the reservoir 102. The capacitance, C, between any two capacitive sensing electrode pairs 106-112—for example the capacitive sensing electrode 108-1 and the capacitive sensing electrode 108-2—can be represented as:

$$C208 = \varepsilon A/d \qquad \text{Eq. (1)}$$

where $\varepsilon$ is a constant, A is an area of overlap between the capacitive sensing electrodes 108-1 and 108-2, and d is the distance between the capacitive sensing electrodes 108-1 and 108-2. From (1) it can be seen that the measured capacitance C208 decreases as the distance d increases between the capacitive sensing electrodes 108-1 and 108-2. As the area A and the constant c is known, once the capacitance C208 is measured, the distance between the capacitive sensing electrodes 108-1 and 108-2 can be determined. Once the distance between each of the capacitive sensing electrode pairs 106-112 is known, a fill volume of the reservoir 102 can be determined.

Figure 3:
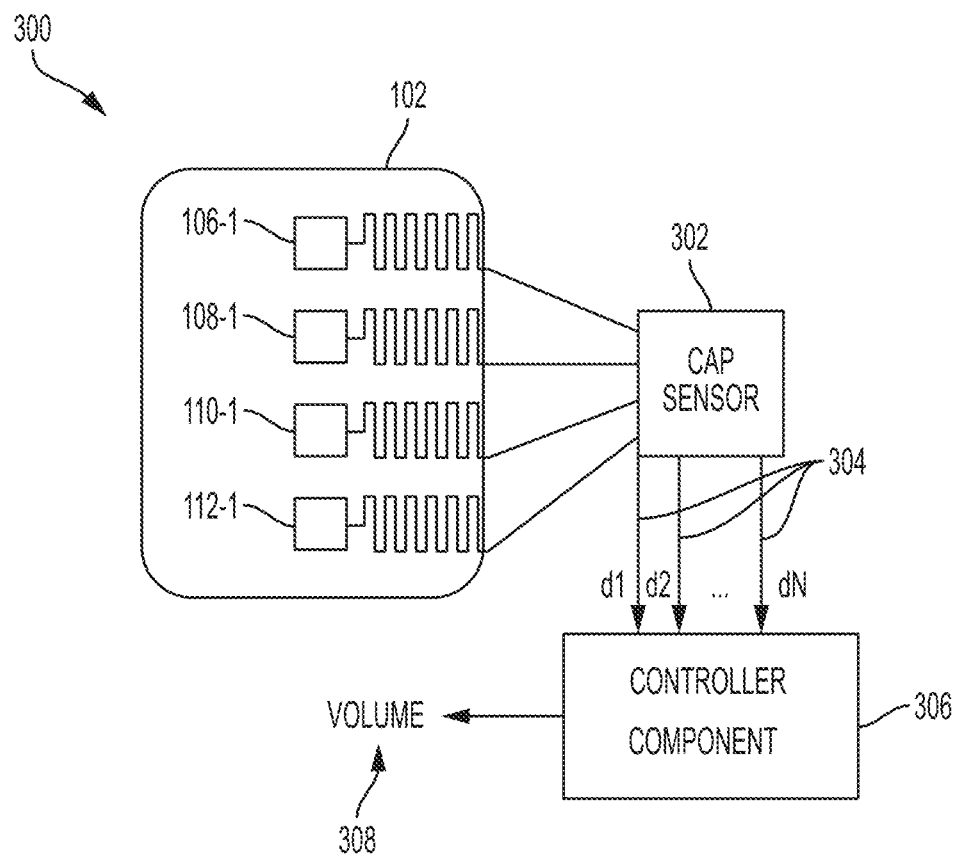
FIG. 3 illustrates an example of a system for determining a fill volume of the reservoir based on the capacitive sensing electrodes.

FIG. 3 illustrates an example of a system 300 for determining a fill volume of the reservoir 102 based on the capacitive sensing electrodes 106-112. As shown in FIG. 3, the system 300 can include the reservoir 102 and the capacitive sensing electrodes 106-112 (with capacitive sensing electrodes 106-1, 108-1, 110-1, and 112-1 being shown on a first side or surface of the reservoir 102). The system 300 can further include a capacitive sensing component or a capacitive sensor component 302. The capacitive sensing component 302 can be coupled (e.g., electrically coupled) to each of the capacitive sensing electrodes 106-112.

The capacitive sensing component 302 may be operable to measure, detect, and/or determine capacitive values associated with or corresponding to the capacitive sensing electrode pairs 106-112 (e.g., the capacitive values 206-212 shown in FIG. 2). For example, the capacitive sensing component 302 may include hardware devices, firmware and/or software that may, for example, utilize an input voltage and a reference voltage to calculate a capacitance value and a distance between the respective capacitive sensing electrode pairs, such as 106-112. In an example, the capacitive sensing component 302 can generate and/or determine corresponding distance values 304 between the capacitive sensing electrode pairs 106-112 based on the determined capacitive values (shown as distance values d1, d2, . . . dn in FIG. 3).

The example system 300 of FIG. 3 can further include a controller component 306. The controller component 306 may be operable to receive inputs from circuits and perform calculations and determinations based on the received inputs. The controller component 306 may, for example, be a logic circuit, a microprocessor executing programming code, circuitry that is a combination of hardware, software and firmware, or the like. For example, the controller component 306 can receive the detected distance values 304 from the capacitive sensing component 302. The controller component 306 can calculate and/or determine (and output) a determined approximate fill volume 308 based on the detected distance values 304. The controller component 306 can implement or execute a volume calculation algorithm to determine the approximate fill volume 308 based on the determined distance values 304 and, for example, the number, size, spacing, arrangement, and/or positioning of the capacitive sensing electrode pairs 106-112 and/or the shape, size, and/or type of the reservoir 102. In an example, the volume calculation algorithm may utilize a table of distance measures that correspond to known volumes. Such a table may, for example, be generated by filling the reservoir 102 with a known volume and measuring the voltages at the capacitive sensing electrode pairs 106-112. Alternatively, the controller component 306 may use volume calculations based on the information received from the capacitive sensing component 302 to determine the fill volume 308. Regardless of the process used to determine the fill volume, the determined fill volume 308 may be stored in a memory (not shown) and/or be provided to a user device or another individual's device (e.g., parent or healthcare professional) to provide an indication of the amount of fluid 202 remaining or stored in the reservoir 102. Volume may be determined through experimentation using a known volume and measuring a resistance.

Figure 4:
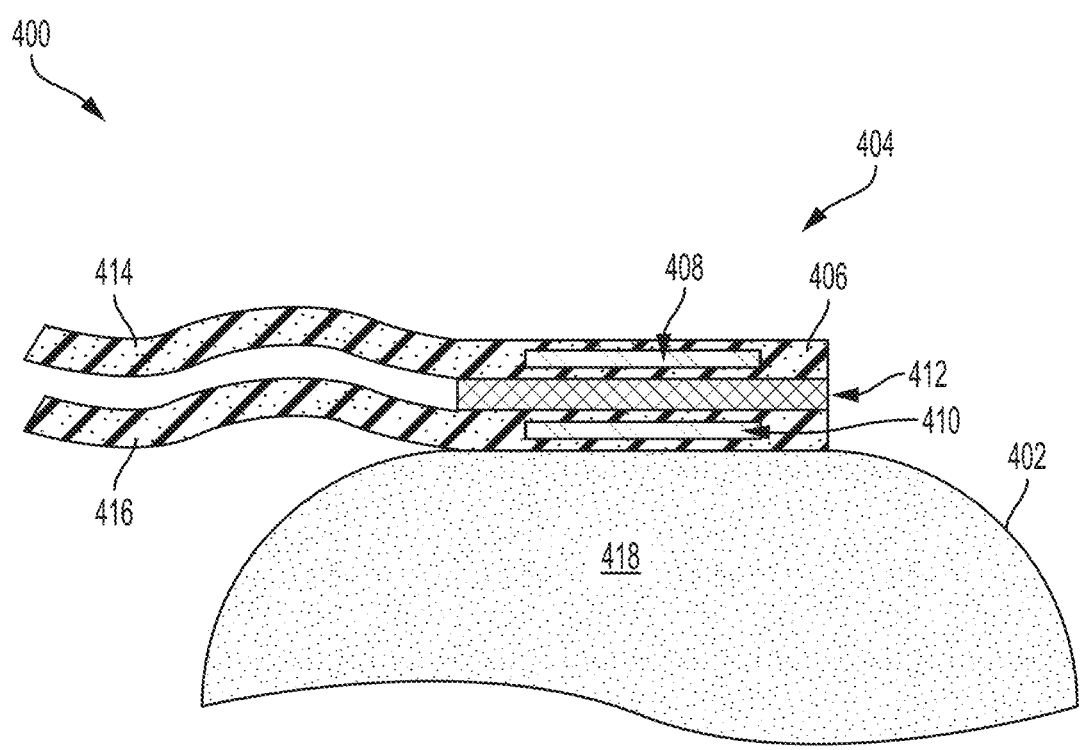
FIG. 4 illustrates an example of a system having a flexible reservoir with imbedded capacitive pressure sensor for fill detection.

FIG. 4 illustrates an example of a system 400 having a flexible reservoir with imbedded capacitive pressure sensor for fill detection. The system 400 can include a reservoir 402 (partially shown in FIG. 4). The reservoir 402 can be a flexible reservoir. In various examples, the reservoir 402 can be made of a plastic material. A shape of the reservoir 402 can change based on an amount of fluid stored in the reservoir 402. A fluid path component (not shown in FIG. 4) can be coupled to the reservoir 402. A liquid or fluid can enter or exit the reservoir 402 through the fluid path component (not shown in this example).

The system 400 can further include a capacitive pressure sensor 404. In various examples, the capacitive pressure sensor 404 can be imbedded in the reservoir 402. In various examples, the capacitive pressure sensor 404 can be positioned on an exterior of the reservoir 402 and/or can be partially disposed within a portion of the reservoir 402. In various examples, the second electrode 410 can be positioned within an interior portion of the reservoir 402 and the first electrode 408 can be positioned on an exterior portion of the reservoir 402.

The capacitive pressure sensor 404 can include a housing 406, a first electrode 408, a second electrode 410, and an elastic material or compliant component 412. The housing 406 can contain the first and second electrodes 408 and 410 and the elastic component 412. The elastic component 412 can be positioned between the first and second electrodes 408 and 410. As shown in FIG. 4, the second electrode 410 can be positioned adjacent to the reservoir 402. A portion of the reservoir 402 can be absent in the area adjacent to the second electrode 410 but is not so limited. In various examples, a portion of the housing 406 can be positioned between the second electrode 410 and the reservoir 102 and/or an interior of the reservoir 402. The housing 406 can be formed from a non-conductive material.

The capacitive pressure sensor 404 can further include a first electrical lead component 414 and a second electrical lead component 416. The first electrical lead component 414 can be coupled to the first electrode 408. The second electrical lead component 416 can be coupled to the second electrode 410. The first and second electrical lead components 414 and 416 can be flexible circuit components and/or can be part of a flexible circuit. The first and second electrical lead components 414 and 416 can be coupled to a controller or other electrical component (not shown in FIG. 4) that can determine a capacitance between the first and second electrodes 408 and 410.

The elastic component 412 can compress as the reservoir 402 is filled with a fluid or liquid (e.g., liquid 418 shown within the reservoir 402), based on increased pressure from filling the reservoir 402. When the elastic component 412 is compressed, a distance between the first and second electrodes 408 and 410 is reduced. As a result, a capacitance between the first and second electrodes 408 and 410 is increased.

The elastic component 412 can be allowed to expand when a stored fluid or liquid within the reservoir 402 is expelled from the reservoir 402, based on the decreased pressure from draining the reservoir 402. When the elastic component 412 expands, the distance between the first and second electrodes 408 and 410 increases. As a result, the capacitance between the first and second electrodes 408 and 410 decreases.

The variable capacitance between the first and second electrodes 408 and 410 can be used to determine a fill volume of the reservoir 402. In particular, an estimate of the amount of fluid within the reservoir 402 can be made based on the capacitance detected or measured between the first and second electrodes 408 and 410. The controller or electrical component coupled to the first and second electrical lead components 414 and 416 can measure and/or detect the capacitance between the first and second electrodes 408 and 410 and can determine a fill volume of the reservoir 102 based on the detected capacitance.

In various examples, the system 400 can include two or more capacitive pressure sensors 404 positioned and/or imbedded within the reservoir 402.

The system 400 can be formed in a variety of ways. In various examples, the reservoir 402 can be formed by blow forming plastic into a large sheet. The large sheet can then be die cut into two halves, with one half having a hole. The two halves can then be heat sealed together, for example, to form the reservoir 402. A flexible circuit comprising, for example, the first and second electrodes 408 and 410 can be laminated on either side of the elastic component 412. The flexible circuit can be adhered to the heat-sealed plastic component or reservoir 402. At this stage, the first and second electrical lead components 414 and 416 can be coupled to the first and second electrodes 408 and 410, respectively, thereby forming the capacitive pressure sensor 404 on or imbedded in the reservoir 402.

Figure 5:
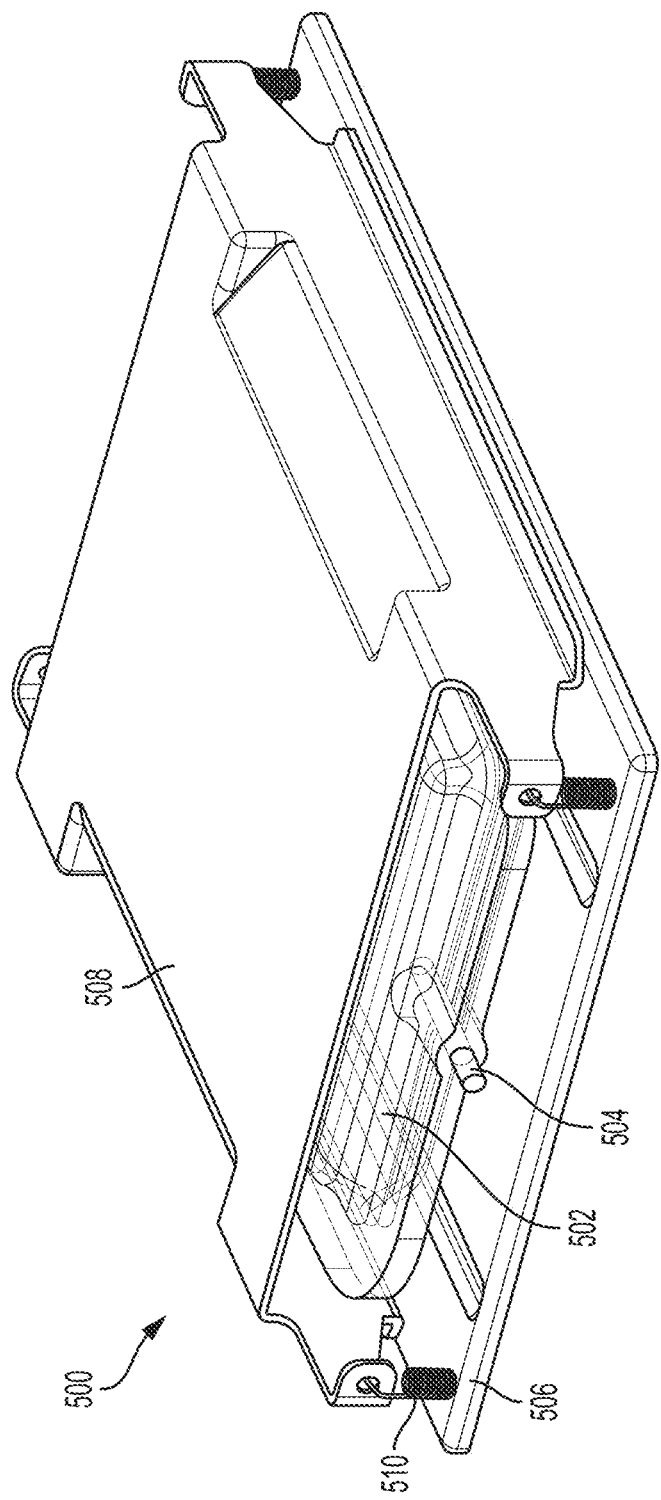
FIG. 5 illustrates an example of a system with a mechanical clamp for fill detection.

FIG. 5 illustrates an example of a system 500 with a mechanical clamp for fill detection. The system 500 can include a reservoir 502 and a fluid path component 504. The reservoir 502 can be a flexible reservoir. In various examples, the reservoir 502 can be made of a plastic material. A shape of the reservoir 502 can change based on an amount of fluid stored in the reservoir 502. The fluid path component 504 can be coupled to the reservoir 102. A portion of the fluid path component 504 can extend into a cavity or interior of the reservoir 502. The fluid path component 504 can be formed of any material including, for example, plastic or metal. A liquid or fluid can enter or exit the reservoir 502 through the fluid path component 504.

As further shown in FIG. 5, the system 500 can also include a first clamp component 506 and a second clamp component 508. The first clamp component 506 can be a rigid clamp top and can be formed of a metal material. The second clamp component 508 can be a rigid clamp bottom and can be formed of a metal material. The first and second clamp components 506 and 508, respectively, can be coupled together by one or more springs 510. In various examples, a spring 510 can be positioned in each corner between the first and second clamp components 506 and 508. The springs 510 can maintain the second clamp component 508 coupled to the first clamp component 506. As shown, an outer portion of the second clamp component 508 is touching or in contact with the first clamp component 506.

The second clamp component 508 can move (e.g., upwards or downwards) relative to the fixed first clamp component 506 as the reservoir 502 is filled or emptied. For example, as the reservoir 502 is filled with a fluid or liquid, the reservoir 502 can push on a lower surface of the second clamp component 508. Once the reservoir 502 is filled with enough of the liquid, the second clamp component 508 can be raised and moved upward and away from the first clamp component 506.

To determine a fill volume of the reservoir 502, one or more techniques can be implemented. As a first example, the first and second clamp components 506 and 508 can be coupled to first and second electrical component leads (not shown in FIG. 5) which can be coupled to a controller or other electrical component (not shown in FIG. 5). When the reservoir 502 is substantially empty of the fluid, the first and second clamp components 506 and 508 can be electrically coupled together (e.g., as shown in FIG. 5). The controller component coupled to the first and second clamp components 506 and 508 can detect when the first and second clamp components 506 and 508 are electrically connected or coupled together. Accordingly, the controller component can determine that the reservoir 502 is substantially empty.

Filling the reservoir 502 with a liquid can cause the second clamp component 508 to move upward and no longer make contact (physical and/or electrical contact) with the first clamp component 506. At the time when contact is no longer made, the controller can determine that the reservoir 502 is being filled and can estimate a fill volume of the reservoir 502. Further, the controller component can be operable to detect a capacitance between the first and second clamp components 506 and 508 as the distance between the first and second clamp components 506 and 508 increases or decreases.

As an example, as the reservoir 502 is being filled, the distance between the first and second clamp components 506 and 508 can increase, resulting in a decreasing capacitance between the first and second clamp components 506 and 508. As the reservoir 502 is being emptied, the distance between the first and second clamp components 506 and 508 can decrease, resulting in an increasing capacitance between the first and second clamp components 506 and 508. The controller component coupled to the first and second clamp components 506 and 508 can detect and/or measure the variable capacitance between the first and second clamp components 506 and 508, to determine a distance between the first and second clamp components 506 and 508. Based on the determined distance, an estimate of the fill volume of the reservoir 502 can be determined and/or an estimate of the amount of liquid within the reservoir 502.

While descriptions have been described as "making electrical contact," capacitive sensing of the proximity of electrodes to one another may be used. In addition, while the capacitive and resistive electrodes or plates are shown as being substantially rectangular, the electrodes may be any shape suitable for enabling the functions and operations described herein to be accomplished.

Figure 6:
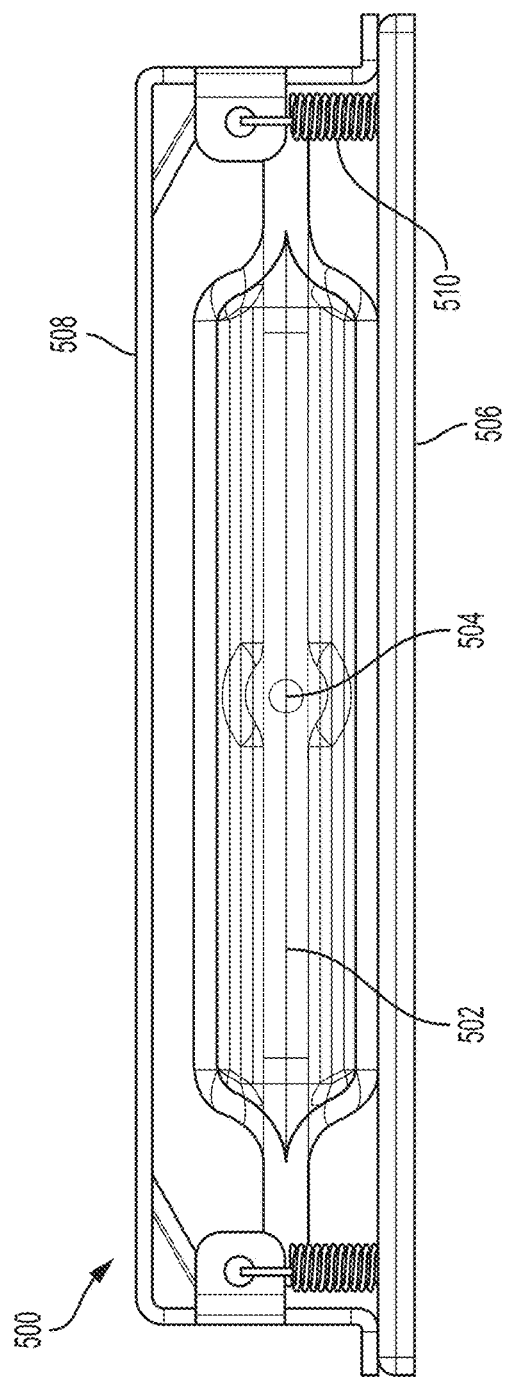
FIG. 6 illustrates a front view of the system.

FIG. 6 illustrates a front view of the system 500. As shown, the fluid path component 504 is coupled to the reservoir 502. Further, the first and second clamp components 506 and 508 are shown in contact with one another. The springs 510 are shown as coupling the first and second clamp components 506 and 508 together. The reservoir 502 can be substantially empty as shown in FIG. 6. FIG. 6 shows the relative positioning of the first and second clamp components 506 and 508.

Figure 7:
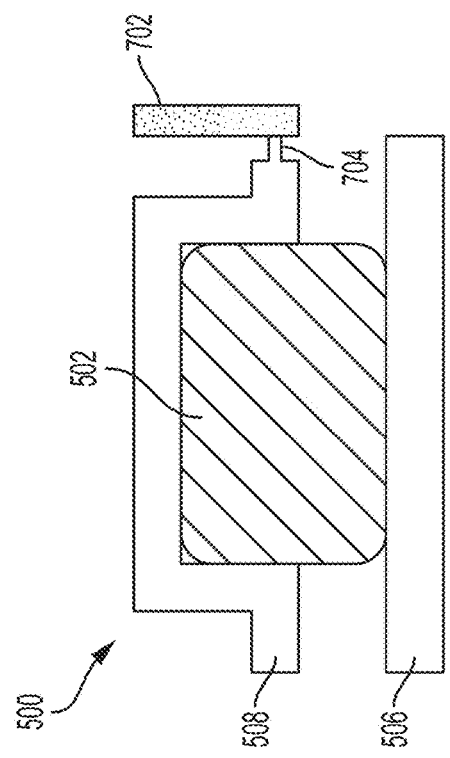
FIG. 7 illustrates the system with a variable resistive component positioned adjacent to the second clamp component.

As an alternative to detecting fill volume of the reservoir 502 by detecting the capacitance between the first and second clamp components 506 and 508, fill volume can be determined based on a detected resistance. FIG. 7 illustrates an example of the system 500 with a variable resistive component 702 positioned adjacent to the second clamp component 508. The variable resistive component 702 can be formed of a material having a variable resistance such as, for example, a carbon paste.

The variable resistive component 702 can be coupled to the controller component by a third electrical lead component (not shown in FIG. 7). The variable resistive component 702 can also be coupled to the second clamp component 508 by an extension component 704 of the variable resistive component 702. The extension component 704 can maintain contact with the variable resistive component 702 as it moves along the variable resistive component 702 (e.g., as it moves up along the variable resistive component 702 as the reservoir 502 enlarges causing the second clamp component 508 to move upward). The controller component can detect a variable resistance value of the variable resistive component 702 based on where the extension component 704 contacts the variable resistive component 702. For example, the variable resistive component 702 can introduce an increasing or decreasing resistance value to a circuit coupled to the controller component as the extension component 704 (and the second clamp component 508) moves up (or down) the variable resistive component 702. The detected resistance value can correspond to a fill volume of the reservoir 502, thereby enabling the controller component to generate an estimate of an amount of fluid contained in the reservoir 502.

In various examples, the second clamp component 508 can be a ratchet guide that allows the reservoir 502 to expand without putting pressure on the reservoir 502. In various examples, in lieu of the one or more springs 510, one or more finger snap components can be used to couple the first and second clamp components 506 and 508 together. The finger snap components can snap into and out of position to allow the first and second clamp components 506 and 508 to be separated without pulling down on the second clamp component 508 as may the one or more springs 510.

The systems, apparatuses, and methods disclosed herein can be used to detect the fill volume of a flexible reservoir including an estimate of an amount of liquid stored in the flexible reservoir. The flexible reservoir can be part of a wearable medical device such as, for example, a wearable insulin delivery device. The systems, apparatuses, and methods disclosed herein can be used to provide a patient or user of the wearable insulin delivery device with an indication via an input/output device of how much insulin is stored in a flexible reservoir and/or how much insulin has been dispensed from a flexible reservoir.

Figure 8:
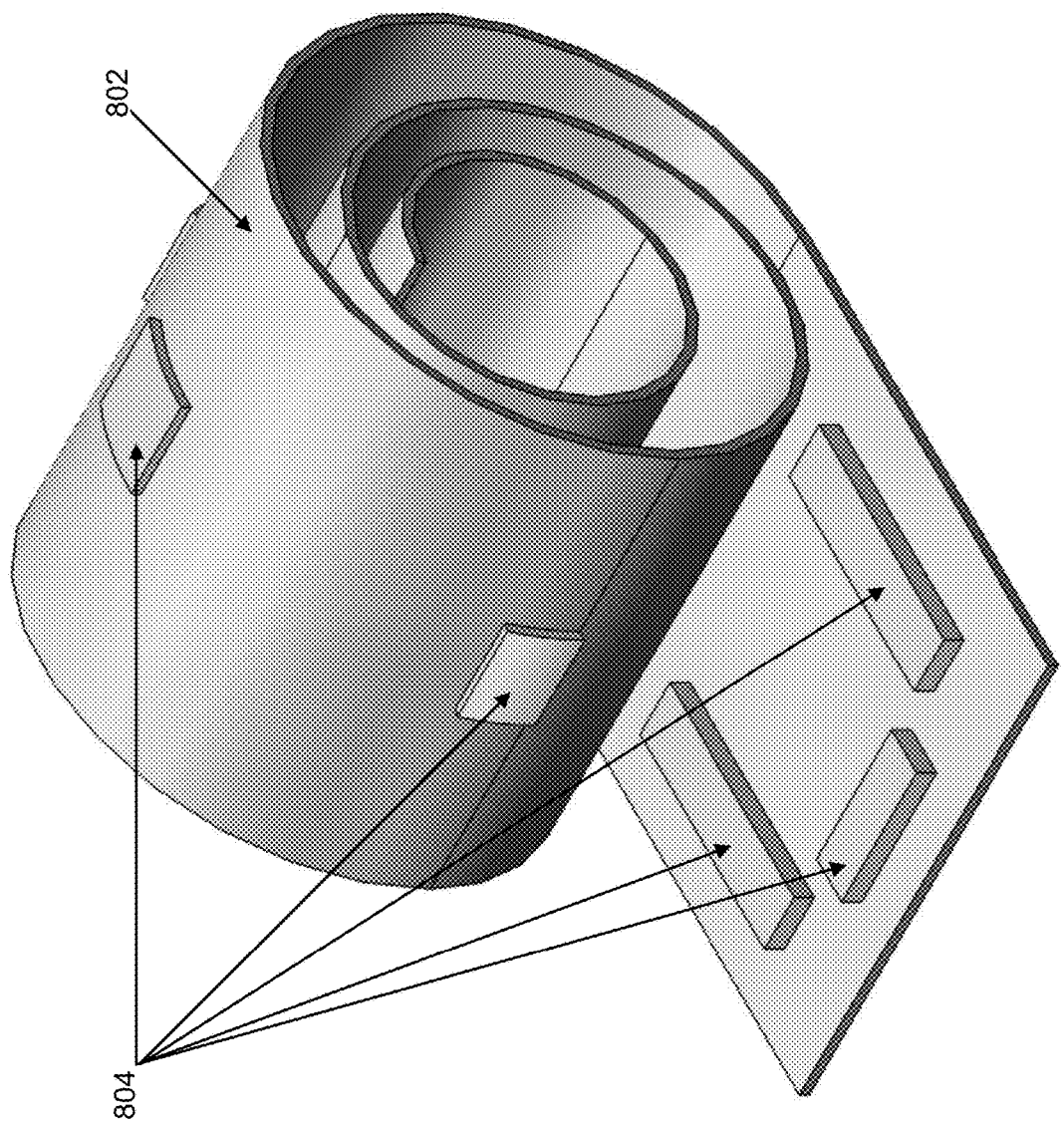
FIG. 8 illustrates a first example of a reservoir system.

FIG. 8 illustrates a first example of a reservoir system. The reservoir system 800 can include a flexible reservoir 802 with selectively arranged electrical contacts 804. FIG. 8 shows the flexible reservoir 802 in an unfilled, rolled-up state. The flexible reservoir 802 can be operable to unroll or unfold as it is filled with a fluid such as, for example, a liquid drug. The electrical contacts 804 can be disposed on the flexible reservoir 802.

The flexible reservoir system 800 can be part of a drug delivery device such as, for example, a wearable drug delivery device. The flexible reservoir 802 can be repeatedly filled and drained of a stored liquid drug. The electrical contacts 804 can be used to sense "wake up" of the flexible reservoir 802—for example, when the flexible reservoir 802 is first initially filled with a liquid drug and first begins to unfold. The electrical contacts 804 can also be used to detect fill volume of the flexible reservoir 802.

Figure 11:
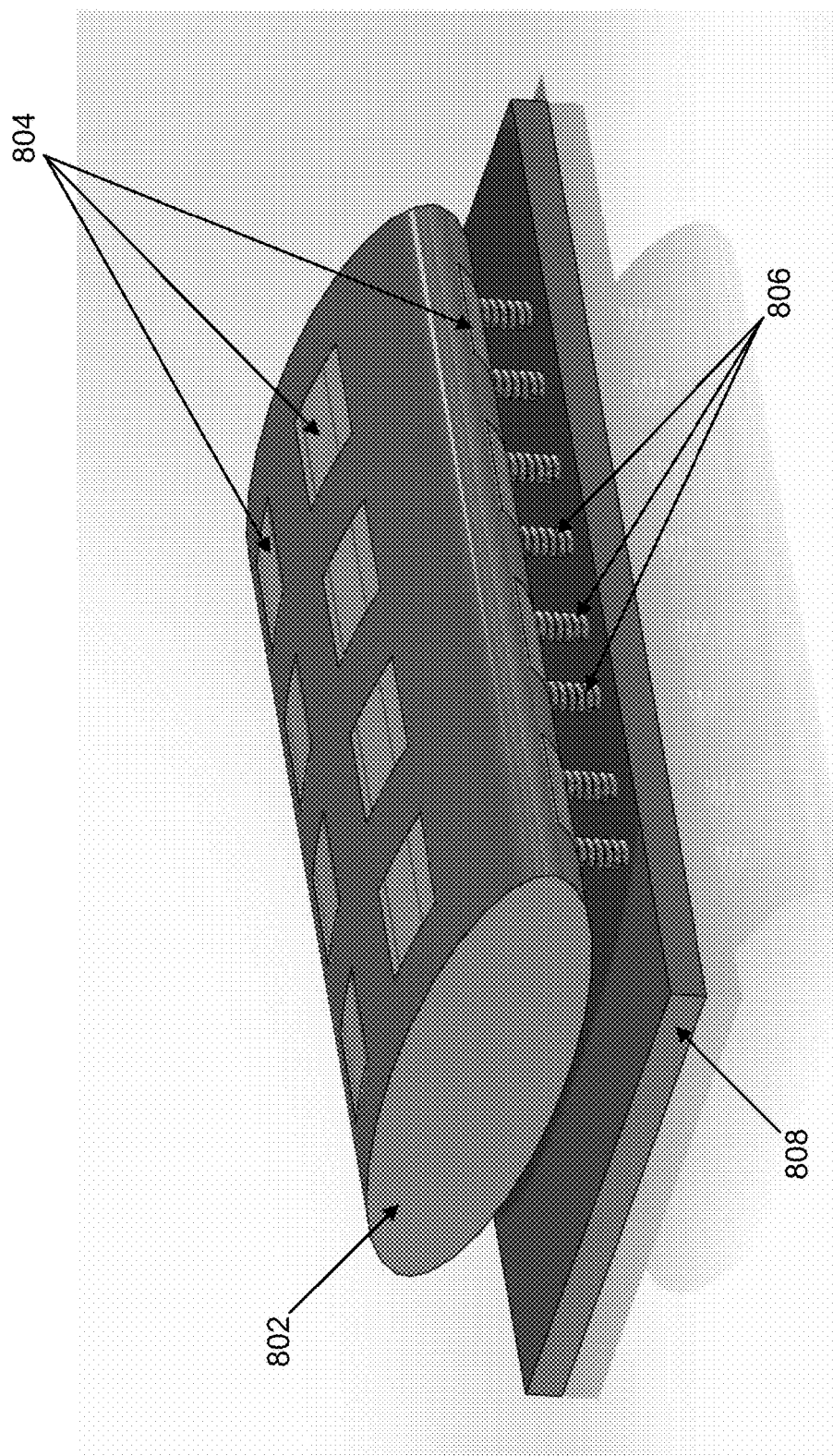
FIG. 11 illustrates the flexible reservoir of the reservoir system of FIG. 8 with a printed circuit board (PCB).

The electrical contacts 804 can have any shape or size. The electrical contacts 804 can be positioned on the top or bottom portions of the flexible reservoir 802 and can be arranged in any manner. As the flexible reservoir 802 is filled and unfolds, the electrical contacts 804 may contact corresponding pins or contacts (shown in other examples) that are separate from the reservoir system 800. As shown in the example of FIG. 11, the corresponding pins can be, for example, positioned on a PCB or other base (or on any component positioned around any portion of the flexible reservoir 802).

As the electrical contacts 804 contact the corresponding pins, an electrical circuit can be completed which may be detected by a controller (e.g., a microprocessor or other logic device). Contact between the electrical contacts 804 and the corresponding pins can be operable to occur sequentially in a predefined manner, based on the unfolding of the flexible reservoir 802 as the flexible reservoir is being filled, such that the controller can determine how much of the flexible reservoir 802 has unrolled which can correspond to a fill volume of the flexible reservoir 802.

In various examples, one or more of the electrical contacts 804 can be used to detect device wake up as the flexible reservoir 802 first begins to unfold. The remaining electrical contacts 804 can be used to facilitate fill volume detection. For example, when the flexible reservoir 802 transitions from an unfilled state to a partially filled state, only certain electrical contacts 804 may make contact (electrical or physical) or mate with their respective contact pins/conductors (shown in another example). The controller can detect that the flexible reservoir 802 has woken up, for example when a first set of contacts 804 interact with a first set of contacts on the PCB and can determine that only a portion of the electrical contacts 804 are mated with their respective contact pins. Based on which electrical contacts 804 are mated with their respective pins and which electrical contacts remain uncoupled to their respective contact pins, the controller can estimate what portion of the flexible reservoir 802 has been filled with the liquid drug, thereby providing an estimate on fill volume for the flexible reservoir 802.

Figure 9:
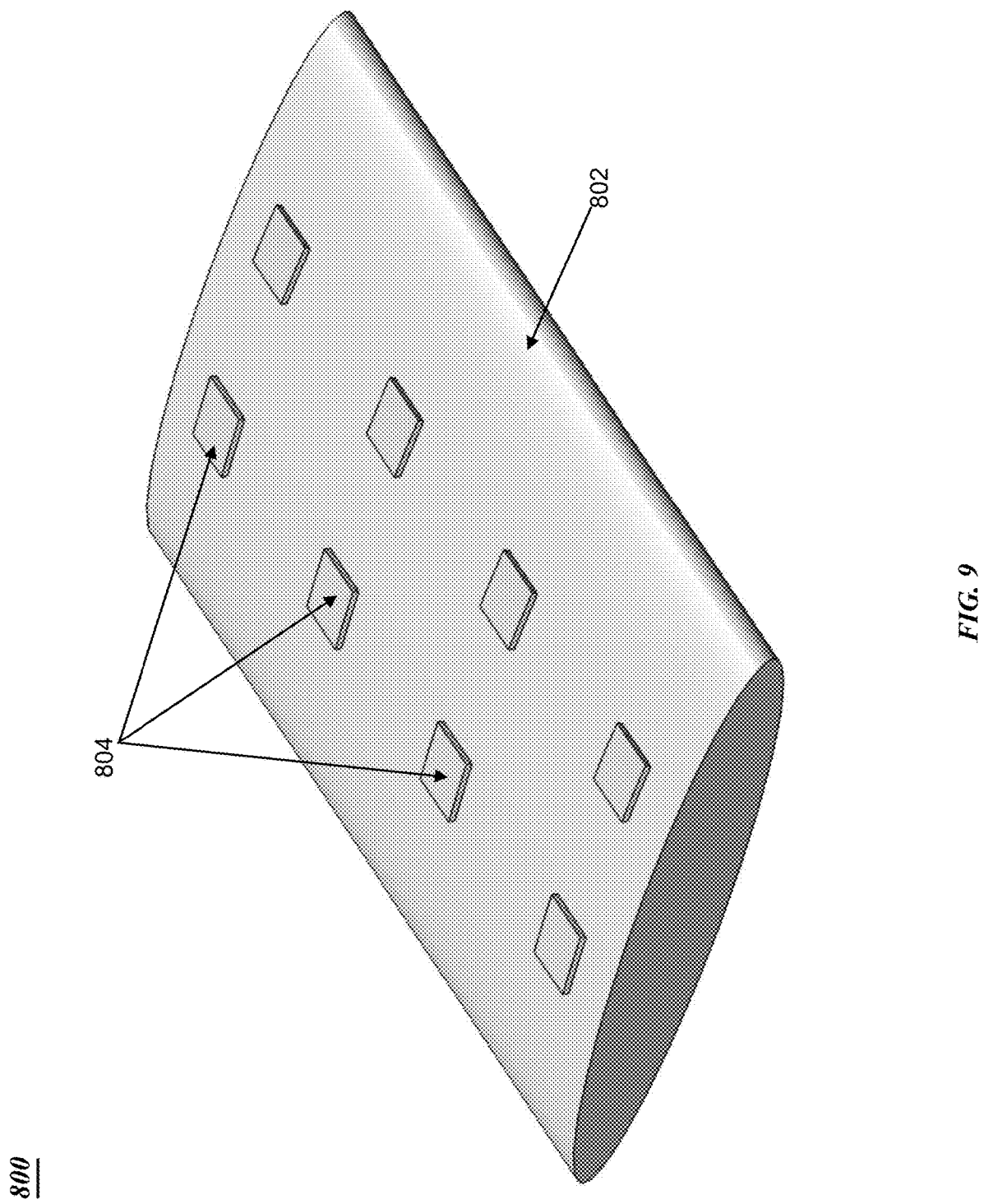
FIG. 9 illustrates a flexible reservoir of the example reservoir system of FIG. 8 in a partially filled state.

FIG. 9 illustrates an example of the flexible reservoir 802 in a partially filled state. One or more select electrical contacts 804 may contact a respective mating pin to indicate to the controller that the flexible reservoir 802 has woken up and is beginning to be filled. These select electrical contacts 804 can trigger initial volume detection operations by the controller. Further, when the flexible reservoir 802 is partially filled, a portion of the remaining electrical contacts 804 can be in contact with respective mating pins, thereby allowing the controller to determine a fill volume of the flexible reservoir 802 based on which electrical contacts 804 are in contact and which are not in contact with respective mating pins.

Figure 10:
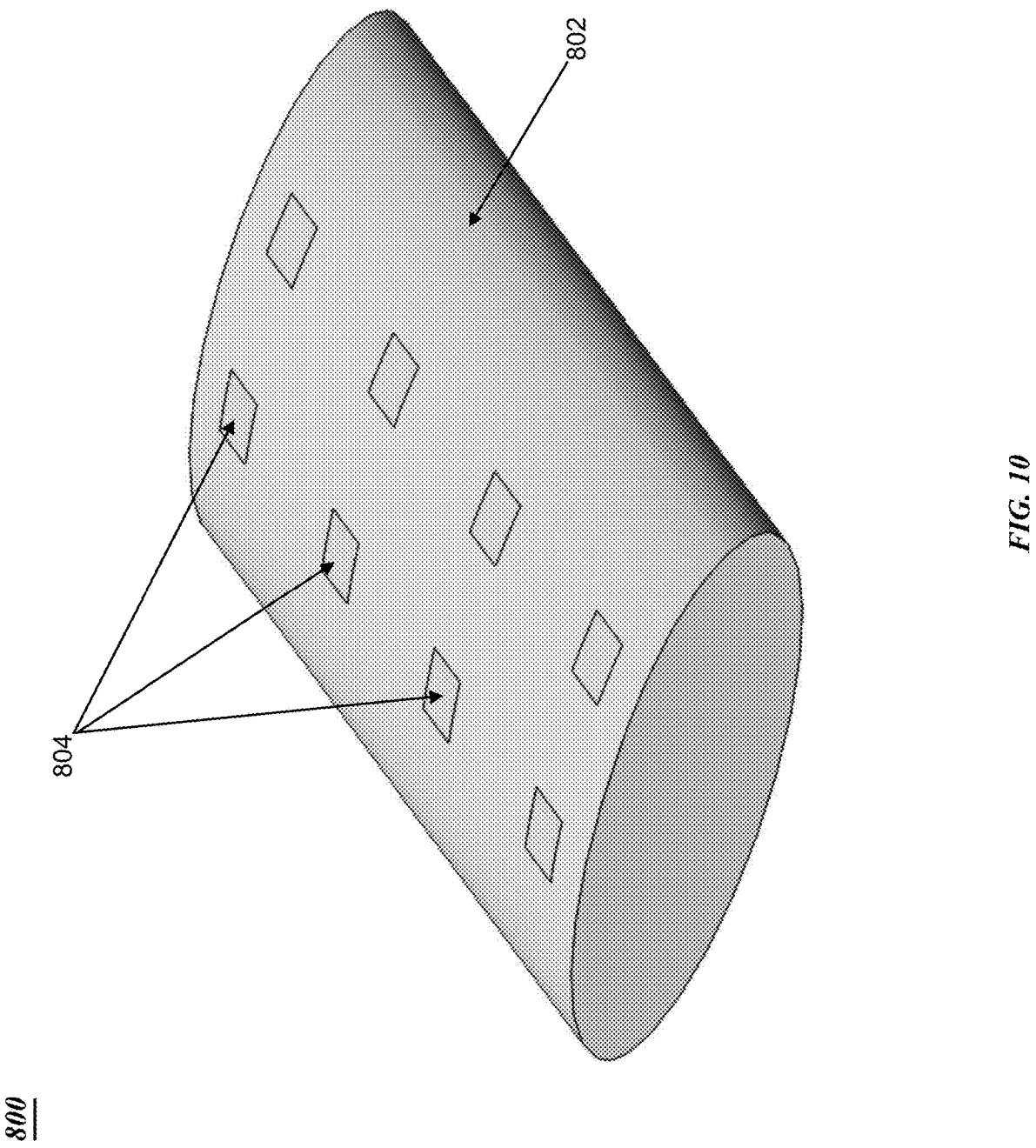
FIG. 10 illustrates the flexible reservoir of the reservoir system of FIG. 8 in a filled state.

FIG. 10 illustrates an example of the flexible reservoir 802 in a filled state. When the flexible reservoir 802 is completely filled, all of the electrical contacts 804 can be coupled to their respective mating pins (not shown in this example). The controller, such as that shown in the example of FIG. 3, can then determine that the flexible reservoir 802 is completely filled. Overall, the shape, geometry, size, and number of electrical contacts 804—along with their corresponding mating pins or contact pads—can be varied and adjusted depending on the design of the flexible reservoir 802 (e.g., the shape and size of the flexible reservoir 802) and/or depending on the accuracy desired to be achieved for fill sensing. Corresponding mating contact pads or pins can be disposed around any portion of the flexible reservoir 802 and may contact electrical contacts 804 positioned on an upper or lower surface of the flexible reservoir 802.

FIG. 11 illustrates an example of the flexible reservoir 802 with a PCB 808. The PCB 808 can include contact pads or pins 806. The contact pins 806 may contact respective or corresponding electrical contacts 804 as the flexible reservoir 802 is filled. As shown in FIG. 11, the contact pins 806 can be arranged to contact the electrical contacts 804 positioned on a bottom portion or underside of the flexible reservoir 802. When contact between an electrical contact 804 and a respective contact pin 806 is made, an electrical circuit can be completed that can be detected by the controller. In various examples, conductive pins can be positioned over the flexible reservoir 802 to contact the electrical contacts 804 positioned on the upper portion of the flexible reservoir 802.

Figure 12:
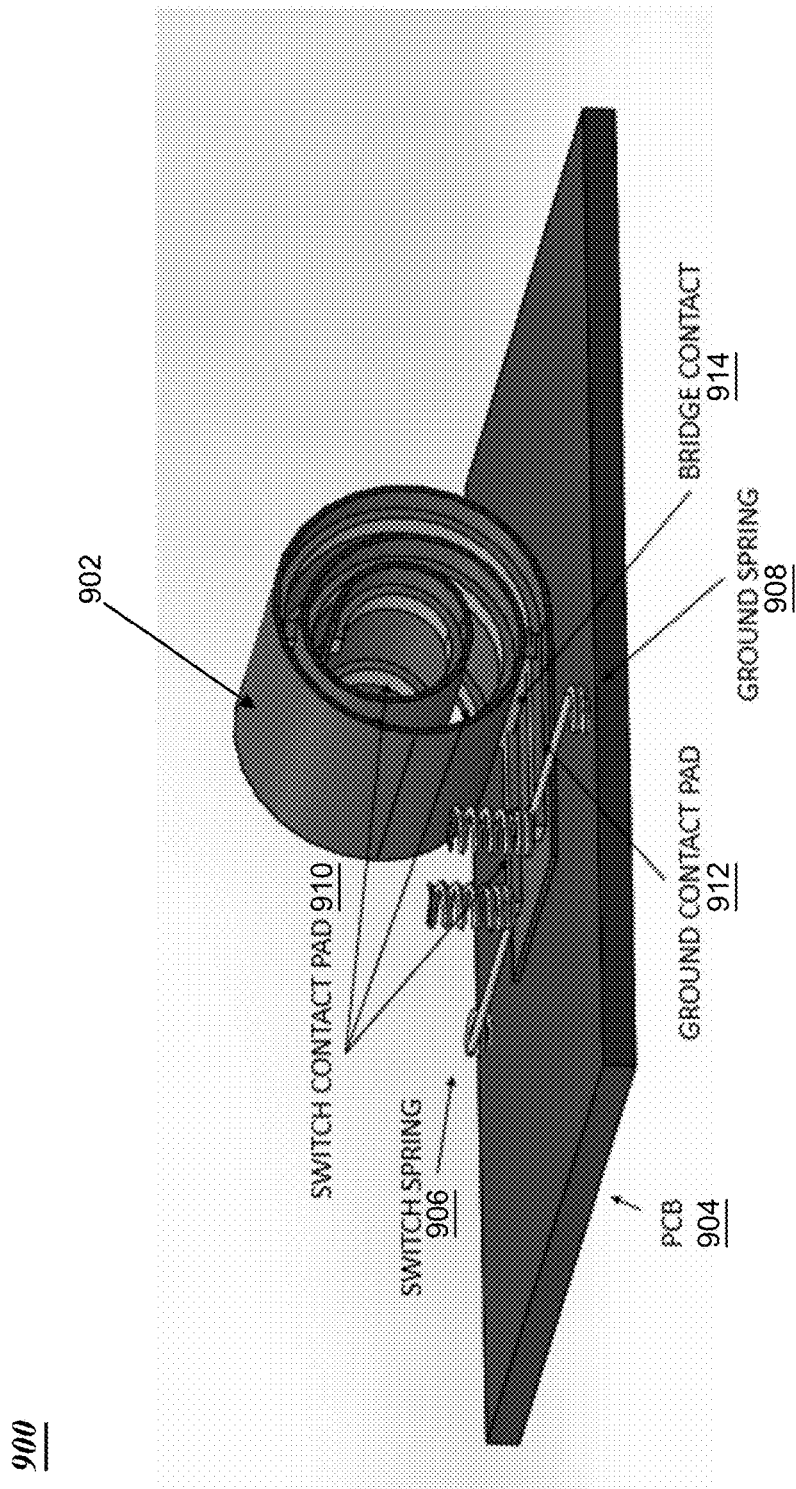
FIG. 12 illustrates a second example of reservoir system.

FIG. 12 illustrates a second example of a reservoir system. As shown, the reservoir system 900 can include a flexible reservoir 902, a PCB 904, a switch spring 906, a ground spring 908, a switch or processor contact pad 910, a ground contact pad 912, and multiple bridge contacts 914. FIG. 12 illustrates the flexible reservoir 902 in an unfilled state.

The flexible reservoir 902 can be positioned on the PCB 904. The switch spring 906 can be coupled to the switch contact pad 910. The switch spring 906 can be coupled to a controller (e.g., a microprocessor or other logic device; not shown in FIG. 12 for simplicity). The switch contact pad 910 can be a continuous electrical contact or pad that is disposed on the flexible reservoir 902 (e.g., on a first side of the flexible reservoir 902). The ground spring 908 can be coupled to the ground contact pad 912 and can also be coupled to the controller and/or to a ground. The ground contact pad 912 can be a continuous electrical contact or pad that is disposed on the flexible reservoir 902 (e.g., on the first side of the flexible reservoir 902).

The controller can detect characteristics of an electrical circuit formed between the switch spring 906, the switch contact pad 910, the ground contact pad 912, and the ground spring 908. An electrical circuit can be formed among these components by positioning of the bridge contacts 914. The bridge contacts 914 can be disposed on a second side of the flexible reservoir 102 (e.g., on a side opposite the positioning of the switch contact pad 910 and the ground contact pad 912). The bridge contacts 914 can couple the switch contact pad 910 to the ground contact pad 912 at multiple locations along the flexible reservoir 102 (e.g., when the flexible reservoir 902 is rolled up).

As the flexible reservoir 902 is filled, the flexible reservoir 902 can unroll or unfold. As the flexible reservoir 902 unfolds, the bridge contacts 914 may sequentially break contact with the switch contact pad 910 and the ground contact pad 912. The controller can be operable to detect when each bridge contact 914 breaks contact (and can detect which bridge contacts 914 remain coupled to the switch contact pad 910 and the ground contact pad 912). By detecting when a particular bridge contact 914 breaks contact, the controller can determine how much of the flexible reservoir 902 has unrolled based on the sequentially broken connections, thereby providing an estimate of the fill volume of the flexible reservoir 102.

In various examples, a constant current can be provided to the switch spring 906. The current can travel a path provided by the switch contact pad 910, the bridge contact 914, the ground contact pad 912 and the ground spring 908. Each time a bridge contact 914 breaks contact with the switch contact pad 910 and the ground contact pad 912, the current must travel further to reach a next bridge contact 914 that connects the switch contact pad 910 to the ground contact pad 912. This "new" circuit may have an increased resistance (due to the current having a longer travel path) which results in a lower voltage sensed by the controller. The controller can correlate the changing voltages with specific bridge contacts 914. Based on the known positions of the bridge contacts 914, the controller can determine how much of the flexible reservoir 902 has unfolded, thereby providing an estimate as to the fill volume of the flexible reservoir 902. In various examples, the switch spring 906 and the ground spring 908 can be other types of contacts and are not limited to springs.

The reservoir system 900 provides an opportunity for more accurate volume sensing while minimizing the number of electrical contacts at the PCB 904. For example, the bridge contacts 914 can be spaced close together to detect multiple break points as the flexible reservoir 902 is filled. The first bridge contacts 914 can be used for wake-up detection—for example, to signal that the flexible reservoir 902 is first being filled. The remaining bridge contacts 914 can provide a means for the controller to estimate fill volume.

As each bridge contact 914 is broken, resistance of the circuit formed by the switch spring 906, the switch contact pad 910, the next connected bridge contact 914, the ground contact pad 912, and the ground spring can increase (e.g., in comparison to the completed circuit that was broken by the closer bridge contact 914 being lifted off of the switch contact pad 910 and the ground contact pad 912). For a given input current (e.g., a constant input current), as the resistance increases, a corresponding drop in output voltage can be detected that can enable the fill volume of the flexible reservoir 902 to be determined. As shown in FIG. 12, the first bridge contact 914 is coupled to both the switch contact pad 910 and the ground contact pad 912. Accordingly, the resistance of the formed circuit is at its lowest value, thereby ensuring the output voltage detected is at its highest value. In various examples, the controller can be coupled to the switch spring 906, which is an electrical contact element. While the foregoing example referred to springs as providing the electrical contact. Other than springs, examples of electrical contact elements or electrical contacts include pogo pins, flexible metallic members, soldered electrical connectors through a board, or the like. Alternatively, the electrical contacts may be replaced with capacitive sensing elements, which may be used to measure a change in a voltage based on a distance between the capacitive sensing elements.

Figure 13:
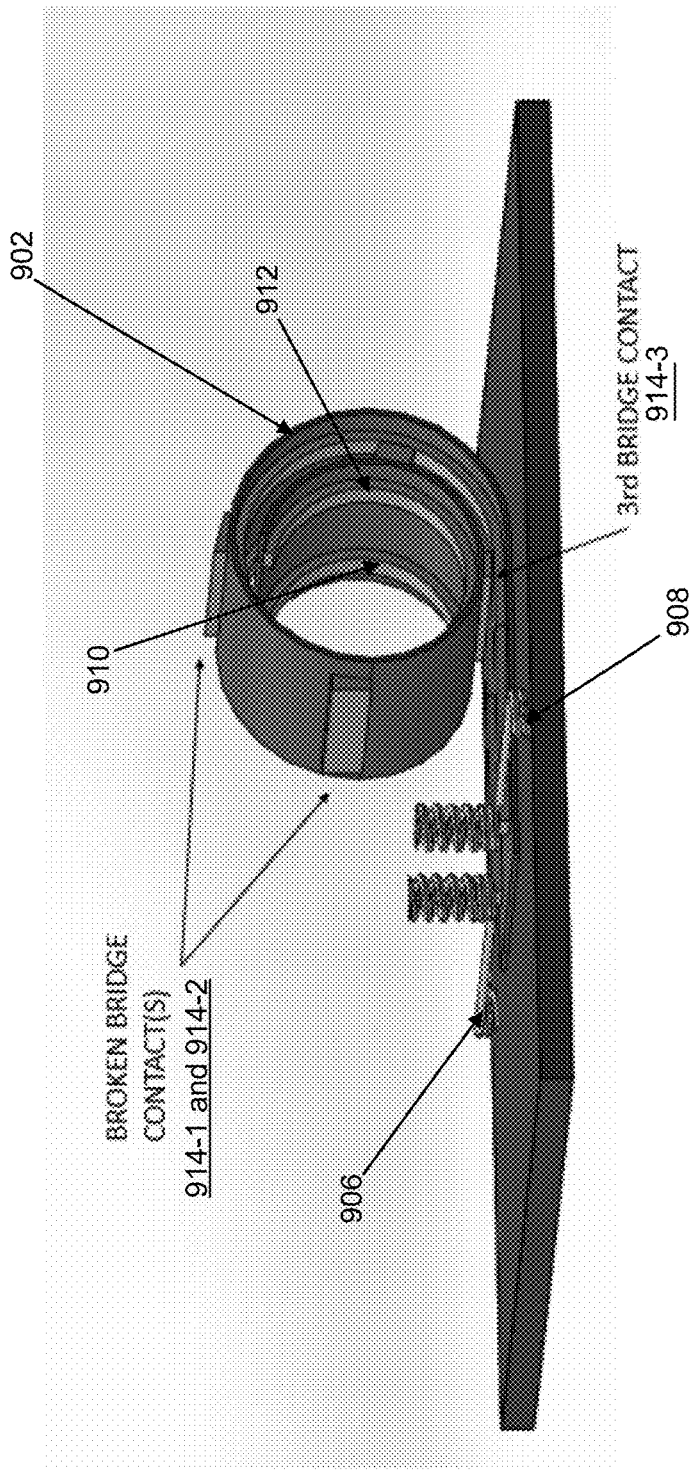
FIG. 13 illustrates a flexible reservoir of the second example of the reservoir system of FIG. 12 in a partially filled state.

FIG. 13 illustrates an example of the flexible reservoir 902 in a partially filled state. As shown, the flexible reservoir 902 is beginning to unfold, causing the first two bridge contacts 914-1 and 914-2 to lift off of the switch contact pad 910 and the ground contact pad 912. The first two bridge contacts 914-1 and 914-2 can be considered to be broken bridge contacts 914. The third bridge contact 914-3 remains coupled to the switch contact pad 910 and the ground contact pad 912.

In comparison to when the first or second bridge contacts 914-1 or 914-2 are connected to the switch contact pad 910 and the ground contact pad 912, current is required to travel further to reach the third bridge contact 914-3. As a result, a measured output voltage can correspondingly decrease. The controller component may measure the voltage changes and can determine fill volume based on the voltage drops. In general, as the flexible reservoir 902 is filled, the flexible reservoir 902 will unroll, causing further bridge contacts 914 to sequentially break connection with the switch contact pad 910 and the ground contact pad 912. For example, a controller component may be coupled to a first contact and a second contact and determine a fill volume of the flexible reservoir as the flexible reservoirs unrolls based on the sequentially broken connections between contacts. Accordingly, the resistance through each new circuit formed after each break increases, causing the output voltage to continue to decrease, which can be translated into fill volume estimations. The fill volume estimations may, for example, be determined apriori by filling the reservoir 902 with a known volume and measuring an output voltage. The measured output voltage may correspond to the respective known volume. This process may repeat for a number of different known volumes.

Figure 14:
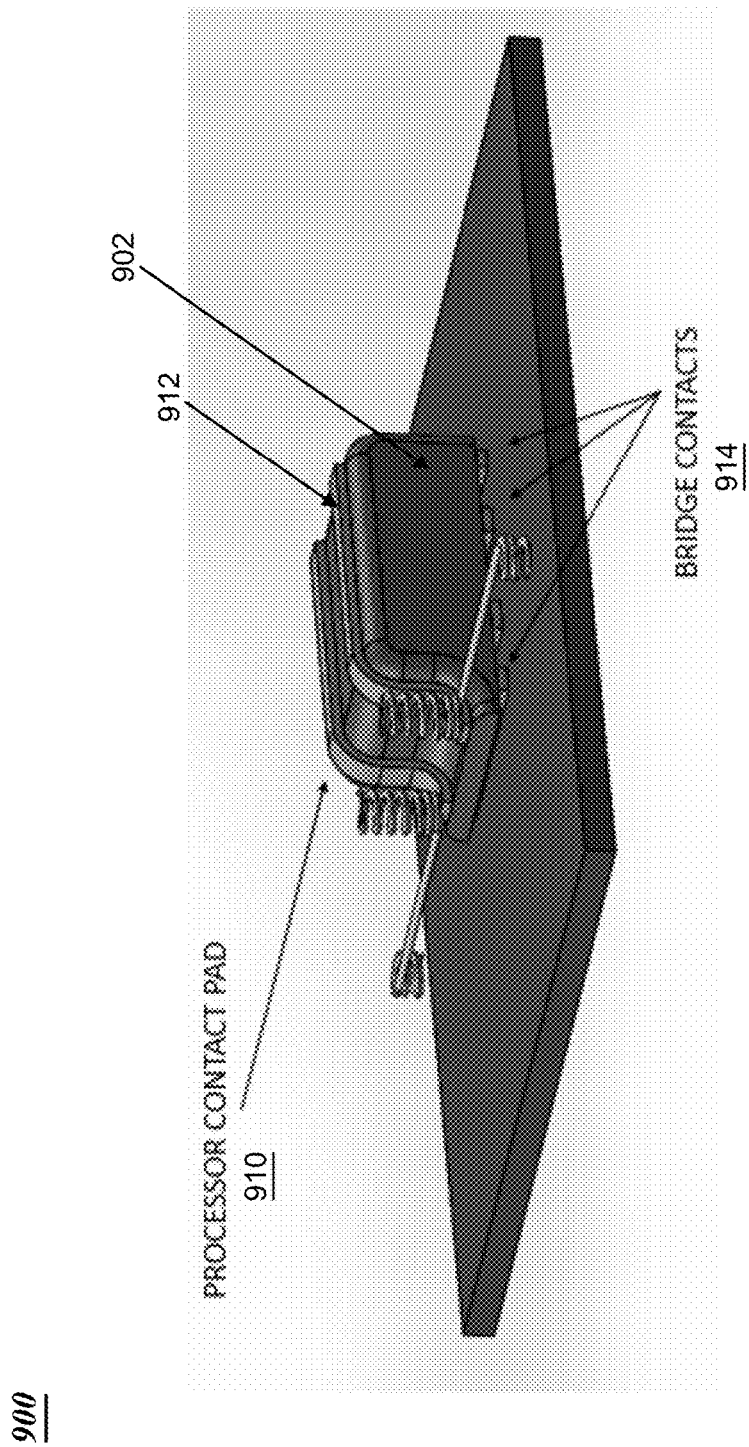
FIG. 14 illustrates the flexible reservoir of the second example of the reservoir system of FIG. 12 in a filled state.

FIG. 14 illustrates the flexible reservoir 902 in a filled state. As shown, the bridge contacts 914 are positioned on an underside of the flexible reservoir 902 and the switch contact pad 910 and the ground contact pad 912 are positioned on a top portion of the flexible reservoir 902. Accordingly, none of the bridge contacts 914 are connected to the switch contact pad 910 and the ground contact pad 912. As a result, no circuit is completed by any bridge contact 914 which can be detected by the controller. The controller can then determine that the flexible reservoir 902 is completely filled based on such information.

Figure 15:
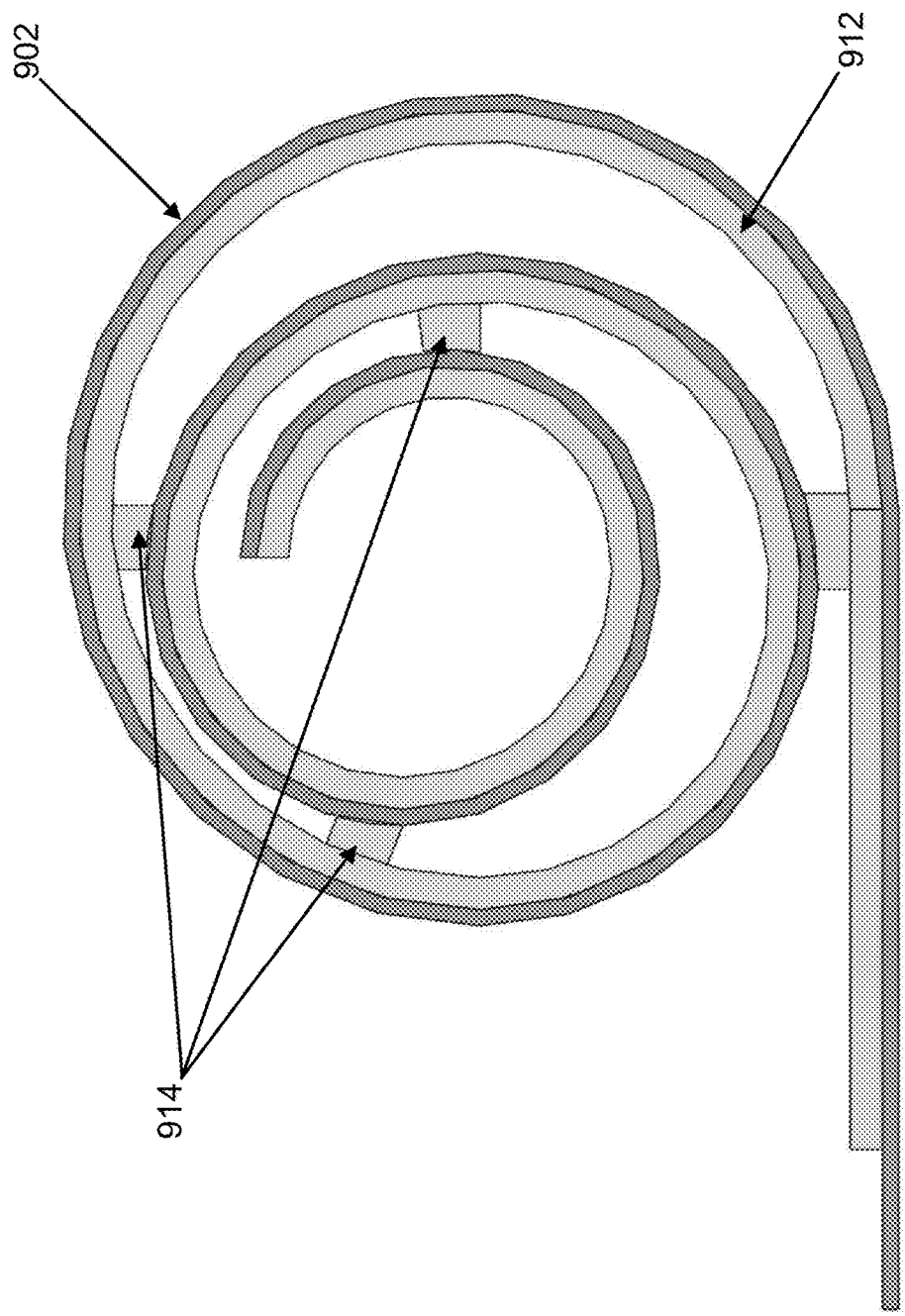
FIG. 15 illustrates a side view of the flexible reservoir of the second example of the reservoir system of FIG. 12.

FIG. 15 illustrates a side view of the flexible reservoir 902. As shown, the flexible is rolled up and empty of a liquid drug. The ground contact pad 912 is shown in contact with multiple bridge contacts 914. As the flexible reservoir 902 is filled, the flexible reservoir 902 will unfold, causing the bridge contacts 914 to sequential break connection with the switch contact pad 910 and the ground contact pad 912. In various examples, the connection of the bridge contacts 914 to the switch contact pad 910 and the ground contact pad 912 can form a resistive network, with each bridge contact 914 connection having a specified designed resistance based on a size and/or a geometry of the completed circuit and/or the components forming the same.

Figure 16:
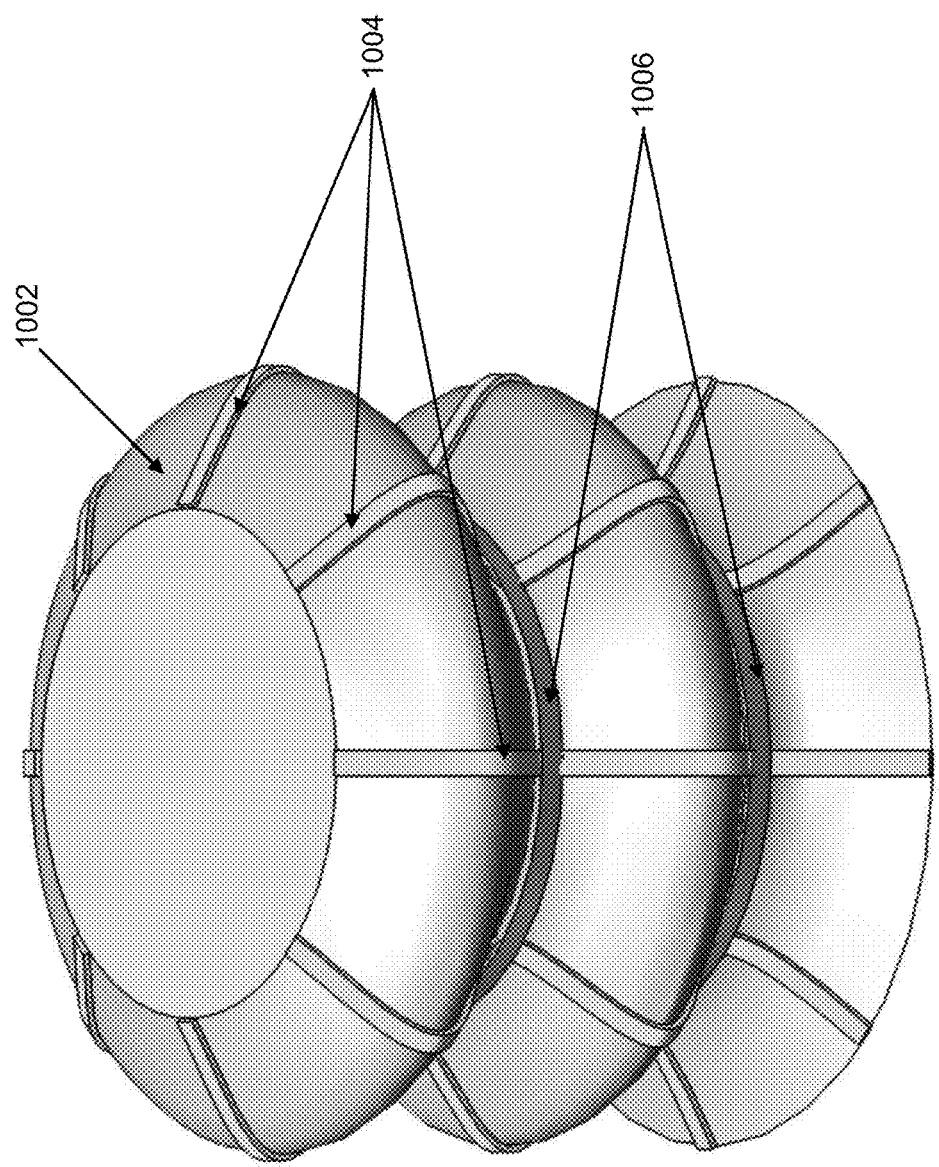
FIG. 16 illustrates a third example of reservoir system.
Figure 17:
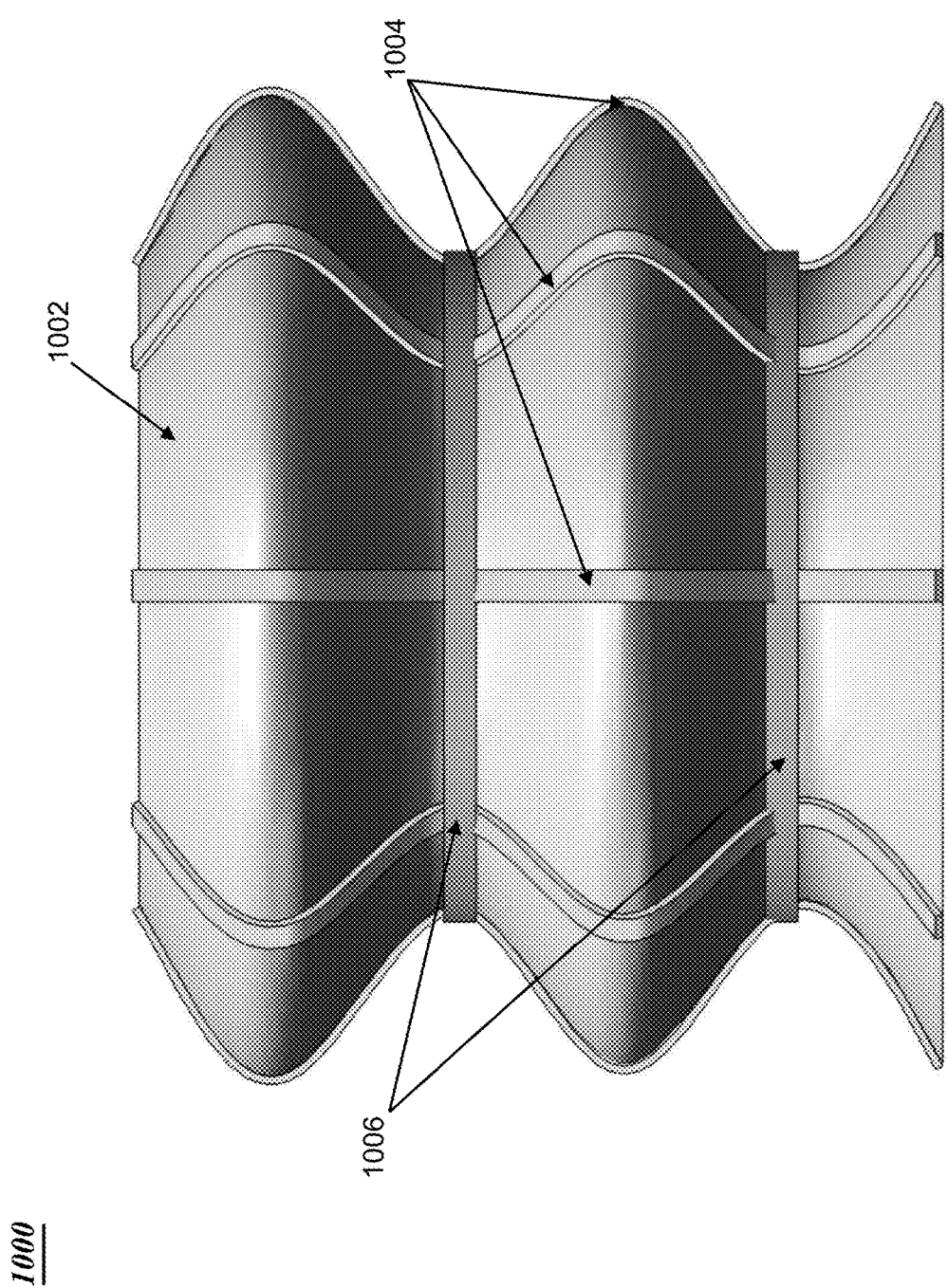
FIG. 17 illustrates a side view of the third example of the reservoir system of FIG. 16.

FIG. 16 illustrates a third example of reservoir system 1000. The reservoir system 1000 includes a bellows style semi-flexible reservoir 1002. The bellows style semi-bellows style semi-flexible reservoir 1002 can inflate or expand in a vertical direction as the bellows style semi-reservoir 1002 is filled. Electrical traces 1004 can be coupled or attached to an outer surface of the bellows style semi-flexible reservoir 1002. The electrical traces 1004 can be arranged around the bellows style semi-flexible reservoir 1002 in a circular pattern and can be spaced apart by the same distance (but are not so limited). Insulating bands 1006 can also be wrapped around the bellows style semi-flexible reservoir 1002 at positions where the bellows style semi-flexible reservoir 1002 can be folded. FIG. 17 illustrates a corresponding side view of the flexible reservoir system 1000.

The reservoir system 1000 can operate in a similar manner as the reservoir system 900 in that the electrical traces 1004 can break connection with other conductors (not shown in FIG. 16 for simplicity) to form higher resistance circuits as the bellows style semi-flexible reservoir 1002 is filled. As connections are broken to form the circuits with increasing resistance, a controller coupled to the electrical traces 1004 and the corresponding conductors can determine a fill volume of the bellows style semi-flexible reservoir 1002 based on the changing electrical characteristics of the formed circuits (e.g., based on a detected decreasing output voltage given a constant input current).

For example, when the bellows style semi-flexible reservoir 1002 is flatter (e.g., less filled), then the electrical traces 1004 can form shorter circuit path lengths than when the bellows style semi-flexible reservoir 1002 is extended (e.g., more filled). The difference in path lengths provided by the electrical traces 1004 (e.g., in conjunction with corresponding connecting pads, pins, or conductors) can be detected by the controller and used to determine fill volume.

In an alternative example, the electrical traces 1004 can be used to make connections to corresponding conductors as the bellows style semi-flexible reservoir 1002 is filled. As new conductive connections are made during filling, the controller can determine fill volume given the known geometry of the bellows style semi-flexible reservoir 1002 and the electrical traces 1004.

In another example, a reservoir, such as 102, 402, 502, 800, 900 or 1000, may be shaped to expand into open areas within a medical device or drug pump, such as those described in U.S. application Ser. No. 15/359,187. For example, a medical device or drug pump that may utilize an example of the flexible reservoirs described herein may have a void that is to be filled with an expanded or filled reservoir. The void within the medical device or drug pump may have irregular shapes, such as a dog-leg shape, L-shape, T-shape or the like. In an example, the configurations of the reservoir examples in FIGS. 8 and 16 may be combined such that the reservoir 800 may have an implementation of the bellows reservoir 1002 affixed to an area near an end of reservoir 800. In an operational example of a reservoir combining the shapes of reservoirs 800 and 1002, the reservoir 800 unrolls as it is filled with fluid and upon substantially unrolling, the bellows reservoir 1002 may begin to fill and expand to fill a vertical space.

An example of an apparatus and process for making the flexible reservoirs, such as 802 and 902, is described with reference to FIGS. 18A, 18B, 19A and 19B. In the example of FIG. 18A, the system 1801 may include guide members 1810 that guide reservoir outer membrane portions 1821 and 1822 together. The guide members 1810 may be wheels or bars suitable to guide and align the reservoir outer membrane portions 1821 and 1822. The electrode layer 1825 may be laser etched or otherwise produced to provide electrodes such as those described with reference to the earlier examples. The guide members 1810 may enable the reservoir outer membrane portions 1821 and 1822 to sandwich the electrode layer 1825 between the respective reservoir outer membrane portions 1821 and 1822. In an example, the reservoir outer membrane portions 1821 and 1822 may be heat sealed together with the electrode layer 1825 in between the respective reservoir outer membrane portions 1821 and 1822 to form a reservoir side member 1830. Alternatively, the reservoir outer membrane portions 1821 and 1822 may be joined together using an adhesive to form a reservoir side member 1830 that does not interfere with the functioning of the electrodes of the electrode layer 1825. As shown in the close-up view, the adhered, heat-sealed, or otherwise held together reservoir outer membrane portions 1821 and 1822 may form a reservoir side element 1836 and the electrode layer 1825 may be formed from a number of separate electrode elements 1835, which are electrical contact elements.

The example of FIG. 18B illustrates an example of a system operable to form a reservoir from a pair of reservoir side members. The system 1802 has guide members 1815 that may be similar to guide members 1810. The guide members 1815 guide a pair of reservoir side members 1830 together to form a reservoir. For example, the pair of reservoir side members may be heat sealed together, for example, to form a reservoir as shown in the examples of FIGS. 19A and 19B.

Figure 19A:
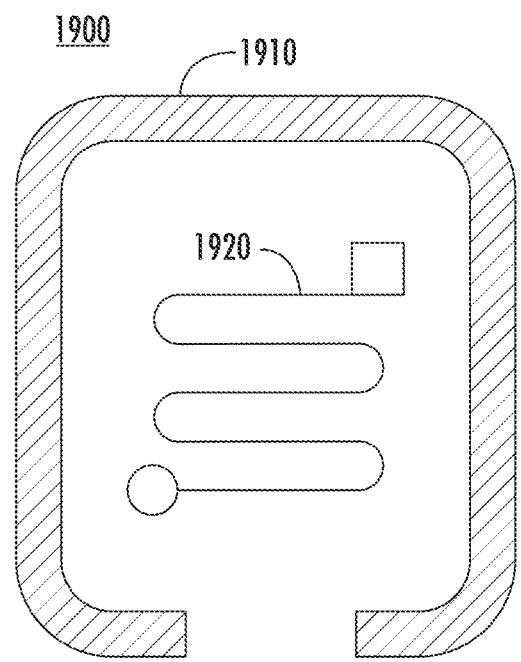
FIGS. 19A and 19B illustrate examples of a completed reservoir having electrodes embedded according to the examples of FIGS. 18A and 18B.
Figure 19B:
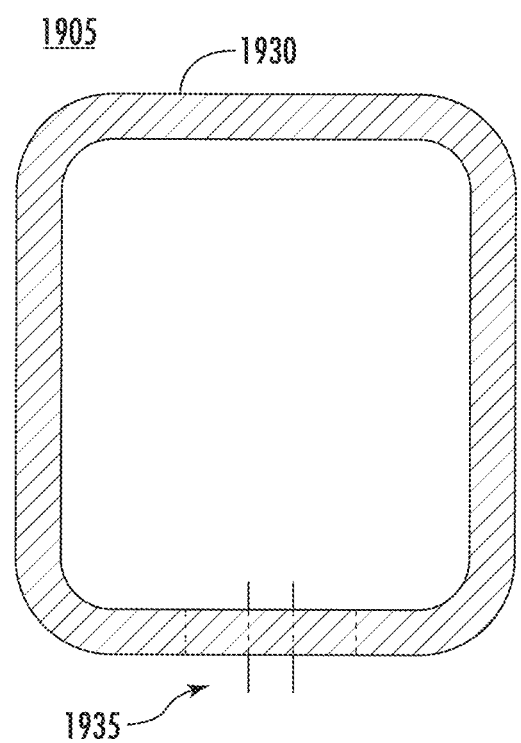

In the examples of FIGS. 19A and 19B, the reservoirs 1900 and 1905, respectively, may be formed from reservoir side members such as 1830. In the example of FIG. 19A, the perimeter 1910 of the reservoir 1900 may be sealed to enable the reservoir 1900 to be filled with fluid, such as insulin. The electrodes 1920 may be arranged in any manner suitable for coupling with a voltage source (not shown). The example of FIG. 19B illustrates a completed reservoir 1905 with a perimeter 1930 that is sealed except for passage 1935, which is used for both filling and emptying the reservoir 1905.

Figure 20:
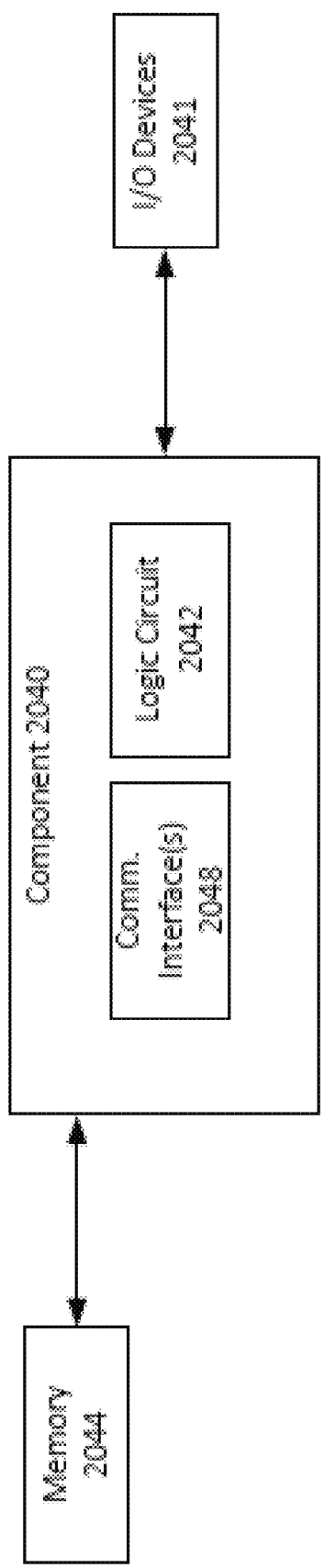
FIG. 20 illustrates an example of a component operable to provide process functions that enable the fill detection operations as described herein.

In an example, such as that shown in FIG. 20, a component 2040 may be implemented in software, but may include hardware or firmware elements. For example, a controller component may include elements such as those shown in component 2040. In the example, component 2040 includes a logic circuit 2042 and one or more communication interface(s) 2048. The logic circuit 2042 may include, one or more processors 2042. Coupled to the component 2040 may be the memory 2044 and one or more input/output (I/O) device(s) 2041. The one or more processor(s) of logic circuit 2042 and communication interface(s) 2048 may be integrated as part of the controller component 2040.

In an example, the memory 2044 can include one or more memory (volatile or non-volatile) devices configured to store instructions used by the logic circuit 2042 to perform one or more operations consistent with the disclosed examples. For example, memory 2044 can be configured with one or more software instructions, such as programs that can perform one or more operations when executed by the logic circuit 2042.

The disclosed examples are not limited to separate programs or computers configured to perform dedicated tasks. For example, memory 2044 can include a single program that performs the operations or could comprise multiple programs. Memory 2044 can also store data that can reflect any type of information in any format that the system can use to perform operations consistent with the disclosed examples.

In the examples, the I/O devices 2041 may be a capacitance sensing device, such as 302 of FIG. 3, an electrode such as 804 of FIG. 8 that provides a voltage value, or the like with respect to the disclosed examples. The component 2040 may also be configured with fewer elements to provide measurements or calculations. For example, the capacitive sensing component 306 of FIG. 3 may be configured similar to component 2040.

The reservoir systems 900 and 1000 can be used as alternative reservoir systems to the reservoir system 100 and can be used within or as part of a wearable drug delivery device. Each of the reservoir systems described herein can provide wake up detection and/or fill volume detection based on making or breaking electrical connections as each system is filled and/or drained of a liquid drug as will be appreciated by one of ordinary skill in the relevant art.

As used in this application, the terms "system" and "component" are intended to refer to a computer-related entity, either hardware, a combination of hardware and software, software, or software in execution. For example, one or more components may be communicatively coupled to each other by various types of communications media (e.g., wired or wireless) to exchange information. For instance, the components may communicate information in the form of signals communicated over the communications media.

Certain examples of the present invention were described above. It is, however, expressly noted that the present invention is not limited to those examples, but rather the intention is that additions and modifications to what was expressly described herein are also included within the scope of the invention. Moreover, it is to be understood that the features of the various examples described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A system, comprising:
a flexible reservoir;
a pair of electrical contact elements operable to contact one another when the flexible reservoir is empty;
a fluid path component coupled to the flexible reservoir; and
a controller component coupled to the electrical contact elements.

2. The system of claim 1, wherein the pair of electrical contact elements include:
a first clamp component positioned under the flexible reservoir; and
a second clamp component positioned over the flexible reservoir.

3. The system of claim 2, wherein the controller component is operable to:
detect a capacitance between the first and second clamp components when the flexible reservoir is filled with a first amount of the liquid;
use the detected capacitance to determine a distance between the first and second clamp components; and
determine a fill volume of the flexible reservoir based the determined distance.

4. The system of claim 2, wherein the second clamp component positioned over the flexible reservoir is operable to move as the flexible reservoir fills.

5. The system of claim 4, wherein the second clamp component is further operable to move away from the first clamp component.

6. The system of claim 2, wherein the first clamp component and the second clamp component are coupled together by one or more springs.

7. The system of claim 2, wherein the second clamp component contacts the first clamp component at an outer portion of the second clamp component.

8. The system of claim 1, wherein a portion of the fluid path component extends into an interior of the flexible reservoir.

9. The system of claim 1, wherein the fluid path component is operable to enable a fluid to enter or exit the reservoir.

* * * * *